US010481684B2

(12) United States Patent
Lopes et al.

(10) Patent No.: US 10,481,684 B2
(45) Date of Patent: Nov. 19, 2019

(54) SYSTEM AND METHOD FOR FOVEATED IMAGE GENERATION USING AN OPTICAL COMBINER

(71) Applicant: NVIDIA Corporation, Santa Clara, CA (US)

(72) Inventors: Ward Lopes, Redwood City, CA (US); Kaan Aksit, Mountain View, CA (US)

(73) Assignee: NVIDIA Corporation, Santa Clara, CA (US)

(*) Notice: Subject to any disclaimer, the term of this patent is extended or adjusted under 35 U.S.C. 154(b) by 0 days.

(21) Appl. No.: 15/815,485

(22) Filed: Nov. 16, 2017

(65) Prior Publication Data
US 2018/0164592 A1 Jun. 14, 2018

Related U.S. Application Data

(60) Provisional application No. 62/432,454, filed on Dec. 9, 2016.

(51) Int. Cl.
G02B 27/00 (2006.01)
G06F 3/01 (2006.01)
(Continued)

(52) U.S. Cl.
CPC .............. G06F 3/013 (2013.01); A61B 3/113 (2013.01); G02B 27/0093 (2013.01);
(Continued)

(58) Field of Classification Search
CPC ........ G02B 7/00; G02B 7/0093; G02B 27/01; G02B 27/0103; G02B 27/0172; G02B 27/0178
See application file for complete search history.

(56) References Cited

U.S. PATENT DOCUMENTS 4,099,841 A 7/1978 Ellis
4,688,879 A 8/1987 Fairchild
(Continued)

FOREIGN PATENT DOCUMENTS

EP 2841991 A1 3/2015
WO 2009126264 A2 10/2009
(Continued)

OTHER PUBLICATIONS

Gramatikov et al., "Directional eye fixation sensor using birefringence-based foveal detection," Applied Optics, vol. 46, No. 10, Apr. 1, 2007, pp. 1809-1818.
(Continued)

Primary Examiner — Darryl J Collins
Assistant Examiner — Journey F Sumlar
(74) Attorney, Agent, or Firm — Leydig, Voit & Mayer, Ltd.

(57) ABSTRACT

A method, computer readable medium, and system are disclosed for generating foveal images. The method includes the steps of redirecting first light rays towards an eye, where the first light rays are redirected by an optical combiner and produce a peripheral image and generating second light rays by a light engine. The second light rays are redirected towards the eye, where the second light rays intersect a first region of the optical combiner and converge at a nodal point within the eye and produce an inset foveal image positioned within at least a portion of the peripheral image. An origin of the second light rays is offset to intersect a second region of the optical combiner in response to a change in a gaze direction of the eye.

20 Claims, 13 Drawing Sheets

(51) Int. Cl.
　　　*A61B 3/113*　　(2006.01)
　　　*G06K 9/00*　　(2006.01)
　　　*G02B 27/01*　　(2006.01)
(52) U.S. Cl.
　　　CPC ..... *G02B 27/0103* (2013.01); *G02B 27/0172* (2013.01); *G06K 9/00604* (2013.01); *G02B 2027/0105* (2013.01)

(56) References Cited

U.S. PATENT DOCUMENTS

| | | | |
|---|---|---|---|
| 5,071,209 | A | 12/1991 | Chang et al. |
| 5,315,417 | A | 5/1994 | Moss et al. |
| 5,325,133 | A | 6/1994 | Adachi |
| 5,610,673 | A | 3/1997 | Rafal et al. |
| 5,684,561 | A | 11/1997 | Yancey |
| 5,808,589 | A | 9/1998 | Fergason |
| 5,861,940 | A | 1/1999 | Robinson et al. |
| 6,027,216 | A | 2/2000 | Guyton et al. |
| 6,351,335 | B1 | 2/2002 | Perlin |
| 6,637,883 | B1 | 10/2003 | Tengshe et al. |
| 6,781,606 | B2 | 8/2004 | Jouppi |
| 6,932,475 | B2 | 8/2005 | Molebny et al. |
| 7,488,072 | B2 | 2/2009 | Perlin et al. |
| 7,747,068 | B1 | 6/2010 | Smyth et al. |
| 7,967,444 | B2 | 6/2011 | Hung et al. |
| 8,094,169 | B2 | 1/2012 | Shimizu |
| 8,529,063 | B2 | 9/2013 | Bonnin et al. |
| 9,040,923 | B2 | 5/2015 | Sprague et al. |
| 9,071,742 | B2 | 6/2015 | Birkbeck et al. |
| 9,582,075 | B2 | 2/2017 | Luebke |
| 9,737,209 | B2 | 8/2017 | Gramatikov et al. |
| 2010/0149073 | A1* | 6/2010 | Chaum .............. G02B 27/0093 345/8 |
| 2012/0307208 | A1 | 12/2012 | Trousdale |
| 2014/0152558 | A1 | 6/2014 | Salter et al. |
| 2016/0033771 | A1 | 2/2016 | Tremblay et al. |
| 2016/0309081 | A1 | 10/2016 | Frahm et al. |
| 2016/0349516 | A1 | 12/2016 | Alexander et al. |
| 2016/0379606 | A1 | 12/2016 | Kollin et al. |
| 2017/0007123 | A1 | 1/2017 | Samec et al. |
| 2017/0014026 | A1 | 1/2017 | Guyton et al. |
| 2017/0075421 | A1 | 3/2017 | Na et al. |
| 2017/0115483 | A1 | 4/2017 | Aleem et al. |
| 2017/0188021 | A1* | 6/2017 | Lo ............................ H04N 3/08 |
| 2017/0196451 | A1 | 7/2017 | Tian |
| 2017/0205876 | A1 | 7/2017 | Vidal et al. |
| 2018/0164880 | A1 | 6/2018 | Kim et al. |

FOREIGN PATENT DOCUMENTS

| | | |
|---|---|---|
| WO | 2016105284 A1 | 6/2016 |
| WO | 2016113533 A2 | 7/2016 |
| WO | 2016160099 A2 | 10/2016 |
| WO | 2017096241 A1 | 6/2017 |
| WO | 2017145154 A1 | 8/2017 |

OTHER PUBLICATIONS

Wang et al., "Pupil and Glint Detection Using Wearable Camera Sensor and Near-Infrared LED Array," Sensors, vol. 15, No. 12, Dec. 2015, pp. 30126-30141.

Mollers, M., "Calibration-Free Gaze Tracking an Experimental Analysis," Diploma Thesis for Computer Science Department at RWTH Aachen University, Nov. 6, 2007, pp. 1-111.

Tobii Tech, "What is Eye Tracking?" 2017, pp. 1-2, as retrieved from https://www.tobii.com/tech/technology/what-is-eye-tracking/.

Aksit et al., "Dynamic exit pupil trackers for autostereoscopic displays," Optics express, vol. 21, No. 12, 2013, pp. 14331-14341.

Ando et al., "Head Mounted Display for Mixed Reality using Holographic Optical Elements," Memoirs—Faculty of Engineering, Osaka City University, vol. 40, 1999, pp. 1-6.

Mukawa et al., "A Full Color Eyewear Display using Holographic Planar Waveguides," SID 08 Digest, Society for Information Display, 2008, pp. 89-92.

Kim et al., U.S. Appl. No. 15/809,849, filed Nov. 10, 2017.

Guttag, K., "Mira Prism and Dreamworld AR—(What Disney Should Have Done?)," Karl Guttag on Technology, 2017, pp. 1-34 retrieved from http://www.kguttag.com/tag/mr/ on Sep. 28, 2017.

Guttag, K., "AR/MR Combiners Part 2—Hololens," Karl Guttag on Technology, Oct. 27, 2016, pp. 1-6.

Altexsoft, "Augmented Reality Check: Get Ready to Ditch Your Smartphone for Goggles," May 26, 2017, pp. 1-18, retrieved from https://www.altexsoft.com/blog/engineering/augmented-reality-check-get-ready-to-ditch-your-smartphone-for-goggles/.

Embitel, "How Combiner Glass in Head-Up Display (HUD) works?," Embitel, May 31, 2017, pp. retrieved from https://www.embitel.com/blog/embedded-blog/how-combiner-glass-in-head-up-display-hud-works.

Hong et al., "See-through optical combiner for augmented reality head-mounted display: index-matched anisotropic crystal lens," Scientific Reports, vol. 7, Jun. 5, 2017, pp. 1-11.

Li et al., "Review and analysis of avionic helmet-mounted displays," Optical Engineering, vol. 52, No. 11, Nov. 2013, 15 pages.

Amitai et al., "Visor-display design based on planar holographic optics," Applied Optics, vol. 34, No. 08, Mar. 10, 1995, pp. 1352-1356.

Guillaumee et al., "Curved Holographic Combiner for Color Head Worn Display," Journal of Display Technology, vol. 10, No. 6, Jun. 2014, pp. 444-449.

Bellini et al., "Virtual & Augmented Reality: Understanding the race for the next computing platform," Equity Research, Jan. 13, 2016, pp. 1-30.

Bekerman et al., "Variations in Eyeball Diameters of the Healthy Adults," Journal of Ophthalmology, vol. 2014, Article ID 503645, 2014, pp. 1-5.

Curran, C., "The road ahead for augmented reality," Apr. 1, 2016, pp. 1-14, retrieved from http://www.pwc.com/us/en/technologyforecast/augmented-reality/augmented-reality-road-ahead.htm.

Merel, T., "Augmented and Virtual Reality to Hit $150 Billion, Disrupting Mobile by 2020," Crunch Network, Apr. 6, 2015, pp. 1-9, retrieved from https://techcrunch.com/2015/04/06/augmented-and-virtual-reality-to-hit-150-billion-by-2020/.

Kim et al., "Analysis of a head-mounted display-type multifocus display system using a laser scanning method," Optical Engineering, vol. 50, Issue 3, Mar. 2011.

Jian-Nan et al., "Key Techniques of Eye Gaze Tracking Based on Pupil Corneal Reflection," Global Congress on Intelligent Systems, IEEE Computer Society, 2009, pp. 133-138.

Sigut et al. "Iris Center Corneal Reflection Method for Gaze Tracking Using Visible Light," IEEE Transactions on Biomedical Engineering, vol. 58, No. 2, Feb. 2011, pp. 411-419.

Lee et al., "Effects of Optical Combiner and IPD Change for Convergence on Near-Field Depth Perception in an Optical See-Through HMD," IEEE Transactions on Visualization and Computer Graphics, vol. 22, No. 5, May 2016, pp. 1540-1554.

Li et al., "Holographic display for see-through augmented reality using mirror-lens holographic optical element," Optics Letters, vol. 41, No. 11, Jun. 1, 2016, pp. 2486-2489.

* cited by examiner

SYSTEM AND METHOD FOR FOVEATED IMAGE GENERATION USING AN OPTICAL COMBINER

CLAIM OF PRIORITY

This application claims the benefit of U.S. Provisional Application No. 62/432,454 titled "Gaze Tracking and Optical Combiner," filed Dec. 9, 2016, the entire contents of which is incorporated herein by reference.

FIELD OF THE INVENTION

The present invention relates to generating foveal images, and more particularly to generating foveal images using an optical combiner.

BACKGROUND

Augmented reality devices have the potential ability to replace desktop monitors and mobile computing platforms (such as smart phones). Augmented Reality (AR) Head Mounted Displays (HMDs) rely on optical elements to combine the images provided by the HMD with the visual information present in the user's environment. As market forces gradually increase the (perceived) resolution requirements, the amount of data to be supplied to the HMD will become prohibitively large. The amount of data that is transferred to the HMD needs to be reduced while the perception of increased image quality is retained. Additionally, conventional HMDs are quite bulky and uncomfortable for a user to wear for several hours. The size and/or weight of the HMD needs to be reduced to enable the HMD to replace a conventional computer display. Thus, there is a need for addressing these issues and/or other issues associated with the prior art.

SUMMARY

A method, computer readable medium, and system are disclosed for generating foveal images. The method includes the steps of redirecting first light rays towards an eye, where the first light rays are redirected by an optical combiner and produce a peripheral image and generating second light rays by a light engine. The second light rays are redirected towards the eye, where the second light rays intersect a first region of the optical combiner and converge at a nodal point within the eye and produce an inset foveal image positioned within at least a portion of the peripheral image. An origin of the second light rays is offset to intersect a second region of the optical combiner in response to a change in a gaze direction of the eye.

DETAILED DESCRIPTION

The size and/or weight of a AR device (e.g., HMD) may be reduced by using an optical combiner to replace the traditional optics that combine images generated by the AR device with the visual information from the user's environment. Optical combiners comprise a holographic optical element (HOE) and can be designed to be virtually transparent to light received from the user's environment (that is, light which does not come from the HMD itself). Therefore, the view for the user will be an unimpeded view of the outside world with the information from the images generated by the HMD added to the view. By configuring the optical combiner to use retinal projection, the optical combiner can be placed closer to the eye than the nearest position where the user can focus. The overall form factor of the resulting device approaches that of prescription glasses and the resulting graphics are perceived by the user to be sharp and in focus.

Conventional optical combiners using non-holographic techniques come in two varieties: video pass through and beam splitters. Video pass through devices use a camera to capture the image of the outside world and then display the captured image to the user after additional information has been added to the image. Compared to optical approaches where the image passes to the user "at the speed of light," the latency inherent in capturing video images of the outside world and then processing the images to add information can be significant and distracting to the user. Furthermore, the processor that performs the image processing must also be close to the HMD requiring either that the HMD is tethered to a nearby stationary computer or that the power requirements for the processor to perform the necessary computations be effectively provided within HMD. The alternate variety of optical combiners, namely, beam splitter devices almost always involve changing the user's perception of her environment. A beam splitter implemented as a wide half silvered mirror prevents a large amount of light from the outside environment from reaching the user's eyes. A dichroic beam splitter also blocks a large amount of light from the outside environment and may change the apparent color of the outside environment. In contrast, an optical combiner implemented with an HOE can be almost completely transparent to light from the user's environment and does not alter the perceived color of the outside environment.

Figure 1A:
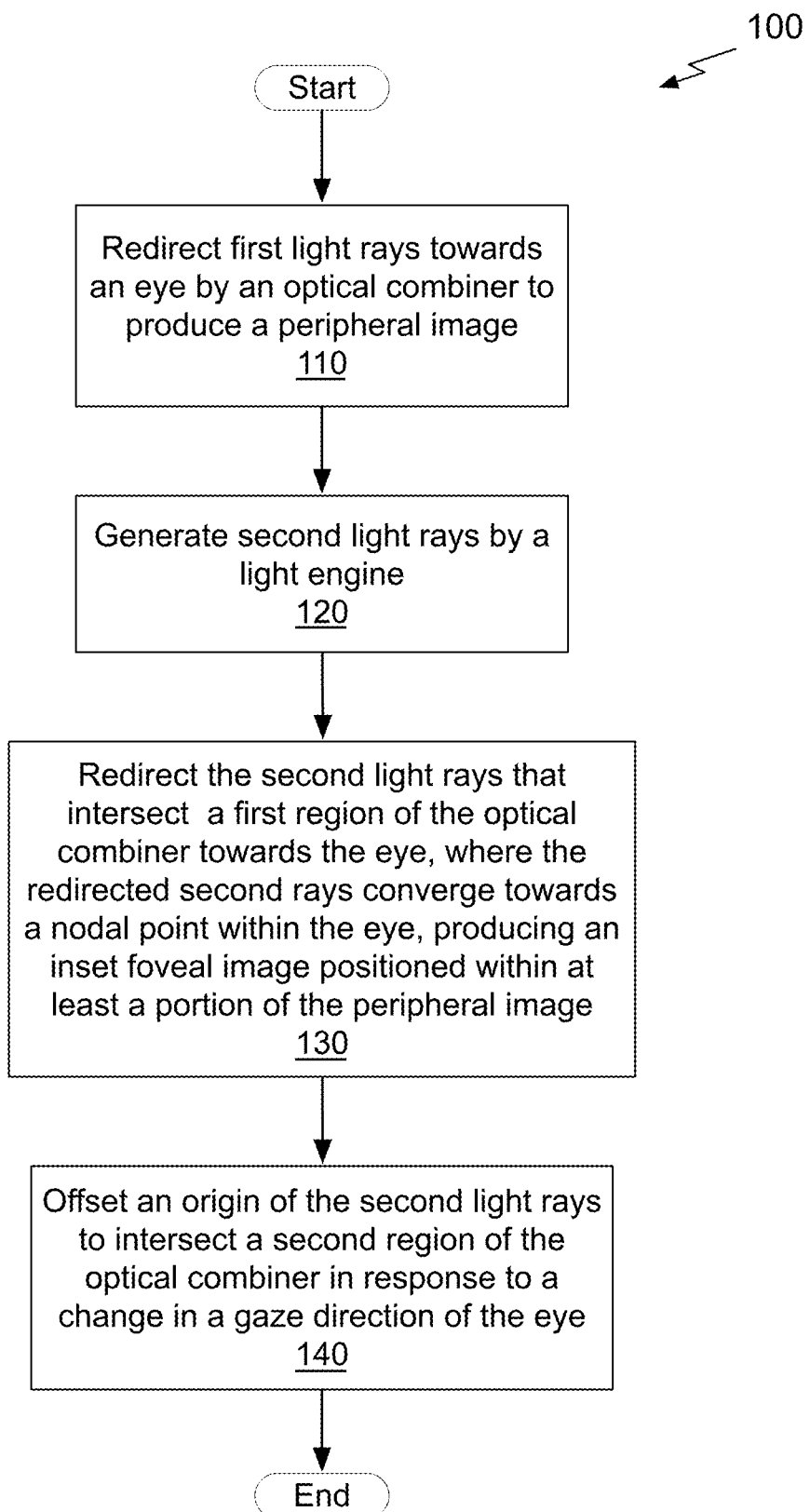
FIG. 1A illustrates a flowchart of a method for generating foveal images, in accordance with one embodiment.

FIG. 1A illustrates a flowchart 100 of a method for generating foveal images, in accordance with one embodiment. Although method 100 is described in the context of a processing unit, the method 100 may also be performed by a program, custom circuitry, or by a combination of custom circuitry and a program. For example, the method 100 may be executed by a GPU (graphics processing unit), CPU (central processing unit), neural network, or any processor capable of generating a foveal image and a peripheral image. Furthermore, persons of ordinary skill in the art will understand that any system that performs method 100 is within the scope and spirit of embodiments of the present invention.

At step 110, first light rays are redirected towards an eye by an optical combiner to produce a peripheral image. In one embodiment, the peripheral image is a low resolution image in terms of the number of samples that are rendered for each pixel. In one embodiment, the optical combiner is a HOE. In one embodiment, the peripheral image is a "background" image covering at least the user's peripheral field-of-view (FOV). In one embodiment, the optical combiner is a HOE having at least two layers, where a first layer redirects the first light rays to generate a peripheral image on the user's retina and a second layer redirects second light rays to generate an inset foveal image on the user's retina. The peripheral image may be lower resolution compared with the inset foveal image. The peripheral image may include a "cutout" where the inset foveal image intersects the peripheral image or the peripheral image may be blurred or have reduced resolution where the inset foveal image intersects the peripheral image. In the context of the following description, any mathematical function may be used to combine the peripheral image and the inset foveal image. In one embodiment, the inset foveal image overlaps at least a portion of the peripheral image. In one embodiment, the inset foveal image and/or the peripheral image is rendered by a processor.

At step 120, second light rays are generated by a light engine. In one embodiment, the light engine comprises a number of projectors that equals the number of HOE layers in the optical combiner, with each projector dedicated to a respective HOE layer. In another embodiment, the light engine comprises a single projector that displays, via time multiplexing, a separate image for each HOE layer in the optical combiner. In yet another embodiment, the light engine generates the peripheral image using a waveguide (using the same projector that generates the inset foveal image or using a dedicated projector). In yet another embodiment, the light engine generates the peripheral image using an emissive display device, where at least a portion of the pixels of the emissive display device present the peripheral image. In one embodiment, the light engine generates the first and second light rays and may be a combination of one or more projectors, waveguides, and/or emissive display devices.

At step 130, the second light rays intersect a first region of the optical combiner and are redirected by the optical combiner towards the eye, where the redirected second rays converge towards a nodal point within the eye, producing an inset foveal image positioned within at least a portion of the peripheral image. In the context of the following description, the inset foveal image is an in-focus image that is centered within the viewer's FOV and combined (i.e., overlaid or inserted) into the peripheral image covering the viewer's peripheral FOV. In the context of the following description, the inset foveal image and the peripheral image are projected onto the user's retina. In one embodiment, the nodal point within the eye is the rotational center of the eye that includes a single point at the precise rotational center of the eye and points within 1 mm of the single point in any direction. In one embodiment, the nodal point within the eye is the geometric center of the eye. In one embodiment, the nodal point within the eye is on the retina of the eye. In one embodiment, the nodal point within a pupil of the eye. In one embodiment, the nodal point is located at any position within the eye.

At step 140, an origin of the second light rays is offset to intersect a second region of the optical combiner in response to a change in a gaze direction of the eye. The optical structure of the eye is aligned about the optical axis of the eye that originates at the retina and passes through the center of the pupil, exiting the eye through the center of the cornea. The optical axis of the eye nearly corresponds to the gaze direction. More specifically, for each individual a constant deviation that is less than or equal to 5° between the optical axis and the gaze direction. When a change in the gaze direction is received, the light engine offsets the origin of the second light rays. In one embodiment, the offset ensures that the optical combiner directs the second light rays to converge at the nodal point within the eye to provide an in-focus image for the changed gaze direction. The in-focus image may be an inset foveal image that is centered within the viewer's FOV and combined (i.e., overlaid or inserted) into the peripheral image covering the viewer's peripheral FOV. In one embodiment, an apparatus provides augmented reality display of a foveated image for an eyeglasses form display device.

More illustrative information will now be set forth regarding various optional architectures and features with which the foregoing framework may or may not be implemented, per the desires of the viewer. It should be strongly noted that the following information is set forth for illustrative purposes and should not be construed as limiting in any manner. Any of the following features may be optionally incorporated with or without the exclusion of other features described.

Figure 1B:
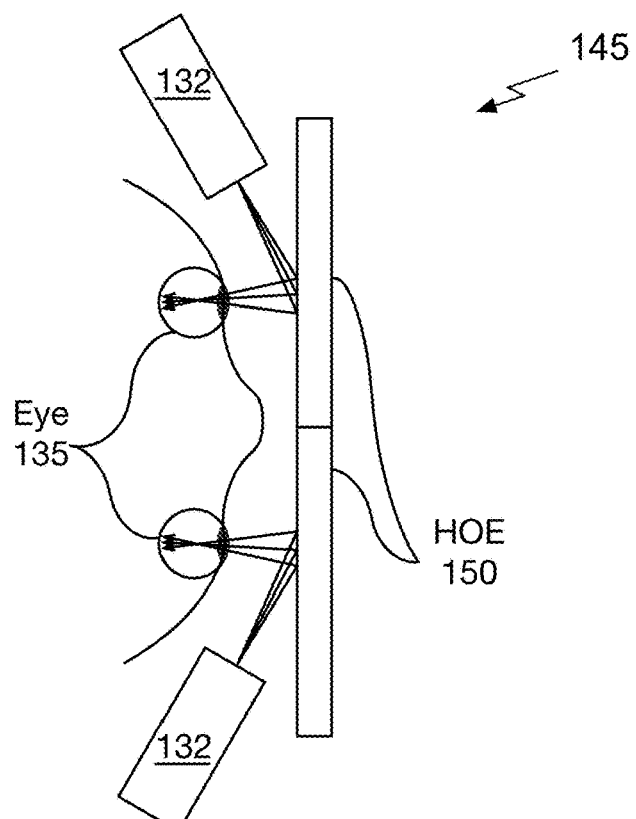
FIG. 1B illustrates a HOE system in a display system, in accordance with one embodiment.

FIG. 1B illustrates HOEs 150 in a display system 145, in accordance with one embodiment. A light engine 132 and HOE 150 correspond to each eye 135 viewed in a top-down cross section of the user's head at approximately, the height of the eyes 135. The light engines 132 and HOEs 150 form the display system 145 that may be included within an eyeglass form factor to function as a HMD device. Because retinal projection is used to generate the images, the HOEs 150 are positioned close to the eyes 135, forming an overall design that is compact. The display system 145 does not suffer from issues of chromatic dispersion or ghost images. There is no need for the user to wear contact lenses to see images with the display system 145. In one embodiment, a single HOE 150 is used for both eyes 135, where separate portions of the single HOE 150 are dedicated to each eye 135.

Each HOE 150 redirects light rays generated by the respective light engine 132 towards a nodal point within the respective eye 135. Each HOE 150 is written (i.e., programmed) to redirect the light rays intersecting the HOE 150 at specific angles for a range of locations (i.e., intersection points) on the HOE 150 towards the nodal point by controlling an angle of reflection. Light rays intersecting the HOE 150 at other angles within the range of locations or outside of the range of locations pass through the HOE 150. As the user's gaze changes, the reflected light rays are redirected, based on the changed gaze direction, to maintain convergence towards the nodal point. As described further herein, although the redirected light rays are redirected towards the nodal point, the redirected light rays do not converge or intersect at the nodal point due to the refractive properties of the eye 135.

Each HOE 150 serves the purpose of replacing one or more optical components (e.g., mirrors, lenses, etc.) in an optical system. HOEs 150 have an advantage of being, generally, lighter and more compact than the optical elements that they replace. The trade-off is that HOEs 150 are typically created for specific purposes and the HOEs 150 are therefore not as versatile as the optical components that are replaced. For example, the HOE 150 that replaces a lens in a particular optical system cannot be simply inserted into a different optical system requiring a lens with the same focal length. The direction of the light rays entering and leaving the HOE 150 must be considered. Like other HOEs, the HOE 150 acts, essentially, as a mapping for light rays that interact with the HOE 150. The HOE 150 maps a small subset of the light rays that intersect the HOE 150 to redirected light rays which leave the HOE 150. A given input light ray with location, direction, and wavelength "programmed" into the HOE 150 at the time of creation of the HOE 150 is mapped to one or more redirected light rays with origins at the point of intersection; but, (almost always) with altered directions compared with the reflected light rays that would be produced by a mirror.

The mapping between input directions and output directions is created is by overlapping beams that have the desired directional properties of the mapping when the HOE 150 is written. Conceptually, to write the HOE 150, two beams (a reference beam and an object beam) are overlapped and form an interference pattern at the location of the holographic medium that becomes the HOE 150. The reference beam contains the set of light rays that intersect the HOE 150 during operation of the display system 145. The object beam contains the set of light rays onto which the light rays from the reference beam are mapped. The interference pattern generated by the interference of the object and reference beams is used to create a diffraction pattern in the holographic medium. The diffraction pattern, thus created, is responsible for the optical properties of the HOE 150. When a light ray that closely resembles a ray in the original reference beam intersects the HOE 150, the light ray is diffracted in the direction of the light ray(s) present in the original object beam at that point of intersection. Full color HOEs 150 are written by creating object and reference beams that contain multiple wavelengths simultaneously, by sequentially exposing holographic media with differently colored laser light, or by stacking multiple single color holograms.

Images generated by the redirected light rays appear sharp and in focus to the viewer. Choices of the locations on the HOE 150 where the light rays generated by the light engines 132 intersect the HOE 150 can affect the size of the eye box (and ease of aligning the hologram with respect to the eyes 135), location of the hologram, effective field of view, the necessity (or not) of eye tracking, and whether the direction of projection will have to account for the gaze direction. In the context of the following description, the eyebox is a viewport volume formed by the light rays that intersect the HOE 150 and are redirected through the pupil of the eye 135. In the context of the following description an intersection angle is an angle at which a light ray intersects the HOE 150. In the context of the following description a reflection angle is an angle at which a light ray that intersects the HOE 150 is redirected towards the nodal point.

Figure 1C:
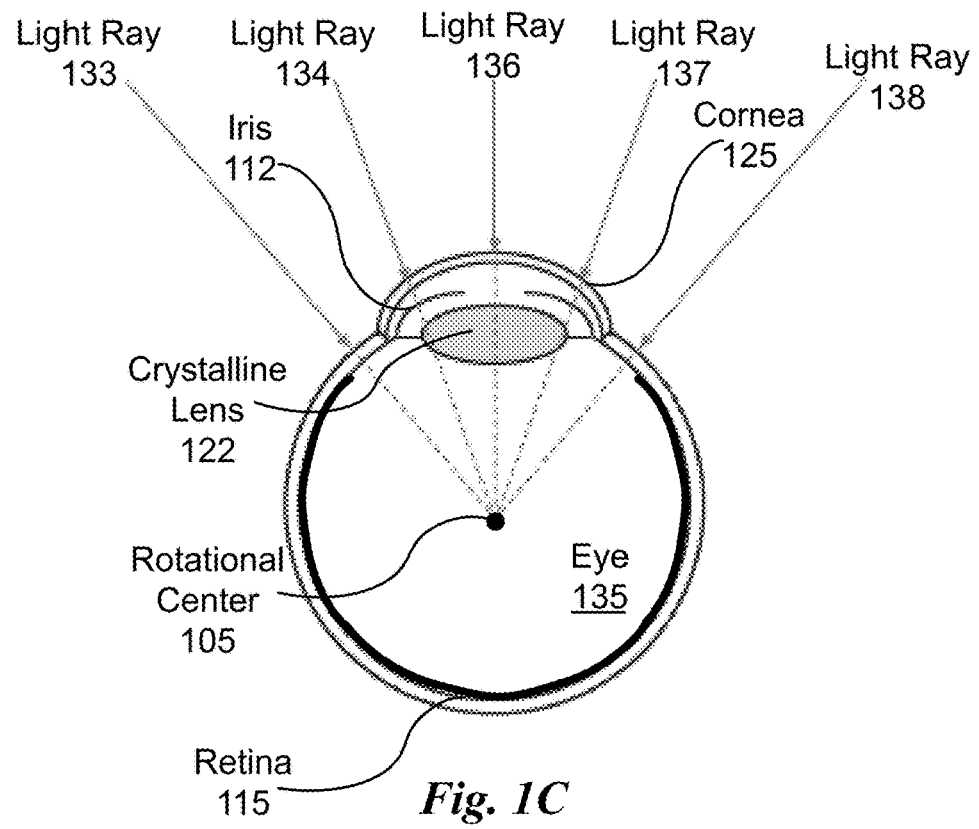
FIG. 1C illustrates a rotational center of the eye, in accordance with one embodiment.

FIG. 1C illustrates a rotational center of the eye 135, in accordance with one embodiment. Overall, the eye 135 is generally spherical. The exception to this shape is the frontal part of the eye 135 that contains the lens structures that focus the image of the outside world onto the back on the eyeball. Specifically, the frontal part of the eye 135 includes a crystalline lens 122, iris 112, and cornea 125. The region between the cornea 125 and crystalline lens 122 is filled with aqueous humor.

Light rays 133, 134, 136, 137, and 138 (shown as arrows) converge towards the rotational center 105 of the eye 135. The light ray 136 enters the eye 135 through a pupil (an opening in the iris 112) and passes through multiple layers having different shapes and refractive indices. The cornea 125 is the medium that the light ray 136 first encounters. The light ray 136 then travels through the aqueous humor and passes through the iris 112 that adjusts the size of the pupil depending on the brightness of the visual scene. Light rays 133, 134, 137, and 138 are occluded by the iris 112. The light ray 136 proceeds to meet the crystalline lens 122 that allows the eye 135 to focus at different distances. Behind the crystalline lens 122 is a liquid, the vitreous humor, which fills most of the eyeball. Finally, the light ray 136 arrives at the retina 115 after passing through the vitreous humor. At the retina 115 some portion of the light is absorbed by the photoreceptors, initiating processing of the visual signal. The unabsorbed portion is diffusively reflected by the retina 115.

As shown in FIG. 1C, the light rays 133, 134, 136, 137, and 138 converge towards the rotational center 105 of the eye 135 form a cone shape. Only a portion of the light rays that are redirected by the HOE 150 in FIG. 1B pass through the pupil and reach the retina 115. The portion of the light rays form a smaller cone shape, so that only the light rays (e.g., light ray 136) within the smaller cone shape reach the retina 115 and form the image that is visible to the user. The optical structure of the eye 135 is aligned about the optical axis of the eye 135 that originates at the retina 115 and passes through the rotational center 105 and pupil and exiting the eye 135 through the center of the cornea 125.

Referring to FIG. 1C, the light rays are directed towards the rotational center 105 of the eye 135 and the gaze direction coincides with the light ray entering through the center of the pupil of the eye 135 (e.g., light ray 136). All other light rays and structure of the eye 135 are rotationally symmetric around the gaze direction. As the user's gaze direction changes, the eye 135 rotates and the light rays that reach the retina 115 change. For example, as the eye 135 rotates clockwise, the light ray 137 passes through the pupil and the light ray 136 is obscured. As the eye 135 rotates counter-clockwise, the light ray 134 passes through the pupil and the light ray 136 is obscured. Assuming that a projected foveal image is centered on the light ray 136, the position of the foveal image should change as the eye 135 rotates so that the foveal image remains visible to the eye 135. The content of the foveal image that is rendered may change accordingly based on the user's gaze direction.

Human eyes can rotate very quickly. Saccades reaching 200 deg/sec of rotation happen commonly, two or three times every second. In the extreme, saccades can easily rotate as fast as 1000 deg/sec during vestibulo-ocular reflex (the counter-rotation of the eyes for maintaining focus on a fixed object while the head is turning). AR devices must react to such fast eye movements immediately for at least two reasons. First, latency is known to be a critical factor for maintaining a user's immersive experience. Second, the computational savings of foveated rendering is closely dependent on how quickly the system responds to the actions of the viewer, i.e. how short the latency is.

Figure 1D:
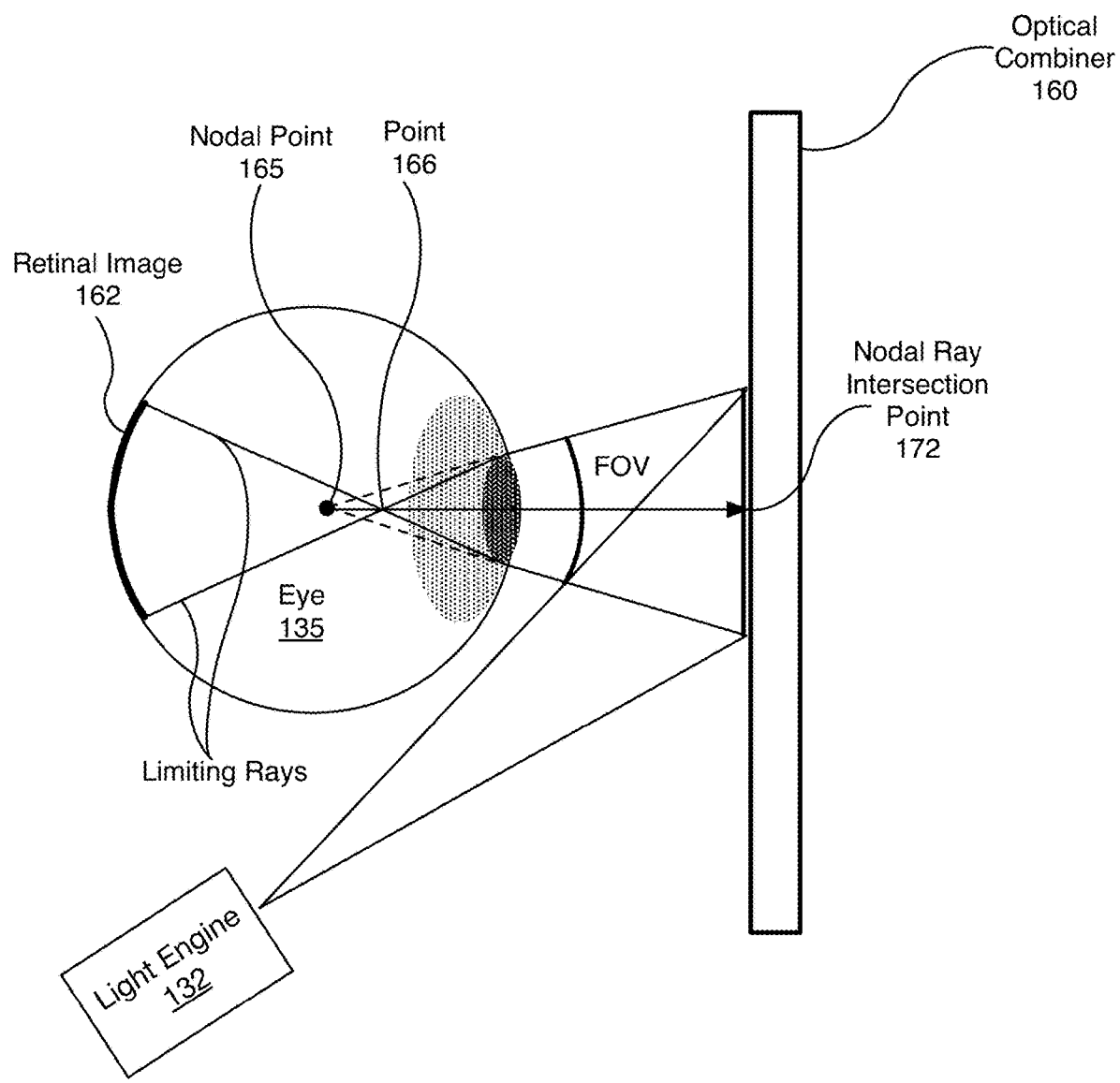
FIG. 1D illustrates an optical combiner system for creating converging rays for the eye and a field of view, in accordance with one embodiment.

FIG. 1D illustrates a portion of the display system 145 of FIG. 1B for creating converging rays for the eye 135 and a field of view (FOV), in accordance with one embodiment. In one embodiment, an optical combiner 160 comprises the HOE 150. The optical combiner 160 changes the direction of light rays that intersect the optical combiner 160 at the programmed intersection angle and at programmed intersection points. The optical combiner 160 is configured to receive a set of diverging light rays and convert the set of diverging light rays into a set of converging light rays. As shown in FIG. 1D, a set of diverging light rays is generated by the light engine 132 and converted, by the optical combiner 160, into the set of light rays that converge towards a nodal point 165 at the rotational center 105 of the eye 135.

The eye 135 is oriented such that the optical axis of the eye 135 (aligned with the rotational center 105 of the eye 135 and the center of the pupil) is perpendicular to the plane of the optical combiner 160. The nodal point 165 is coincident with the rotational center 105 of the eye 135 and a nodal ray intersection point 172 is coincident with the optical axis of the eye 135. Light rays that are redirected by the optical combiner 160, are all directed towards the nodal point 165 on the optical axis of the eye 135. However, upon entering the eye 135, the redirected light rays are refracted and intersect at the point 166. The location where the redirected light rays converge, in the absence of the eye 135 (i.e., ignoring refraction), is the nodal point 165.

As shown in FIG. 1D, a FOV of the eye 135 is limited by the diameter of the pupil. A "central ray" (not shown) propagates along the optical axis from the nodal ray intersection point 172 through the nodal point 165 and two "limiting rays" originate where the pupil meets the iris and terminate at the retina, bounding a retinal image 162. If the focal position of the optical combiner 160 were located further from the eye 135 (i.e., further to the right), given the pupil diameter depicted in FIG. 1D, the FOV would be larger. Therefore, the closer the focal position of the optical combiner 160 to the pupil of the eye 135, the smaller the FOV. The FOV defines a cone shape that is filled with redirected light rays (although only the limiting rays are shown). Ignoring refraction, when each redirected light ray is extended into the eye 135, all of the redirected light rays converge and intersect at the nodal point 165 (as shown by the dotted lines).

Figure 1E:
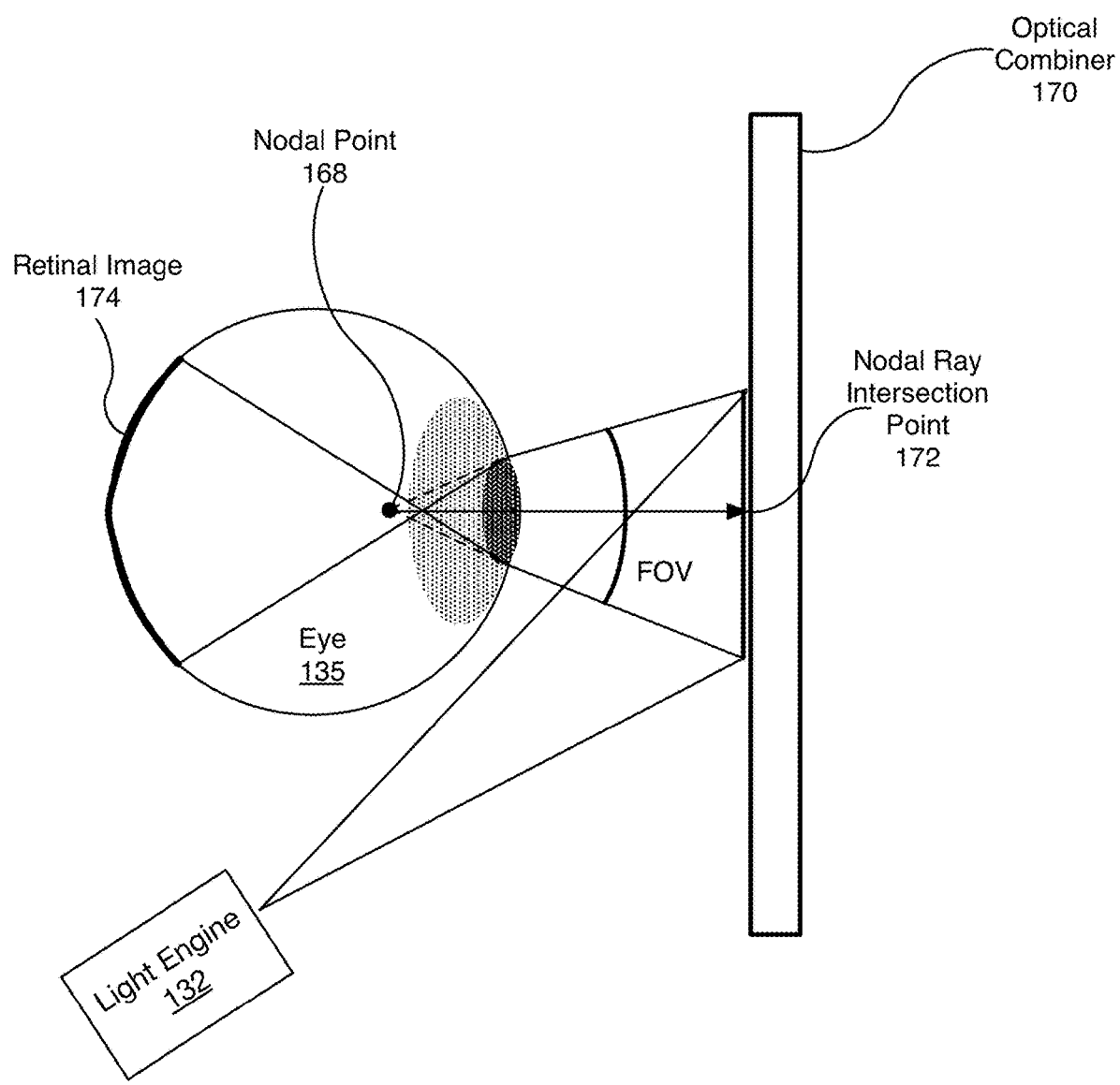
FIG. 1E illustrates the portion of the display system of FIG. 1B for creating converging rays for the eye at a different nodal point compared with the portion of the optical combiner system shown in FIG. 1D, in accordance with one embodiment.

FIG. 1E illustrates the portion of the display system 145 of FIG. 1B for creating converging rays for the eye 135 at a different nodal point 168 compared with the portion of the display system 145 shown in FIG. 1D, in accordance with one embodiment. In one embodiment, the optical combiner 170 is the HOE 150 that is written to redirect light rays generated by the light engine 132 to converge at the nodal point 168. The nodal point 168 is located within the eye 135, but not at the rotational center 105. Compared with the FOV for the optical combiner 160, the FOV for the optical combiner 170 is larger and a retinal image 174 is larger than the retinal image 162. The larger FOV is achieved by configuring the optical combiner 170 (via writing) to redirect the light rays to converge at the nodal point 168.

In one embodiment, an optical combiner 170 is a HOE having at least two responses, where a first response directs the light rays intersecting the optical combiner 170 at a first range of locations to the nodal point 168 and a second response directs the light rays intersecting the optical combiner 170 at a second range of locations to the nodal point 165 (shown in FIG. 1D). In one embodiment, the first response is configured within a first layer of a multi-layer HOE and the second response is configured within a second layer of the multi-layer HOE. In one embodiment, both the first and second responses are configured within respective dedicated locations of a single layer HOE.

A depth of field effect may be achieved (independent of rendering) by producing images that are projected by the light engine 132 and are redirected by the optical combiner 160 to different nodal points, such as the nodal points 165 and 168. As previously described, an HOE having at least two responses may be used, where each response corresponds with a different nodal point. The light engine 132 may employ either time multiplexing or a separate projector for each nodal point to generate the images.

Figure 2A:
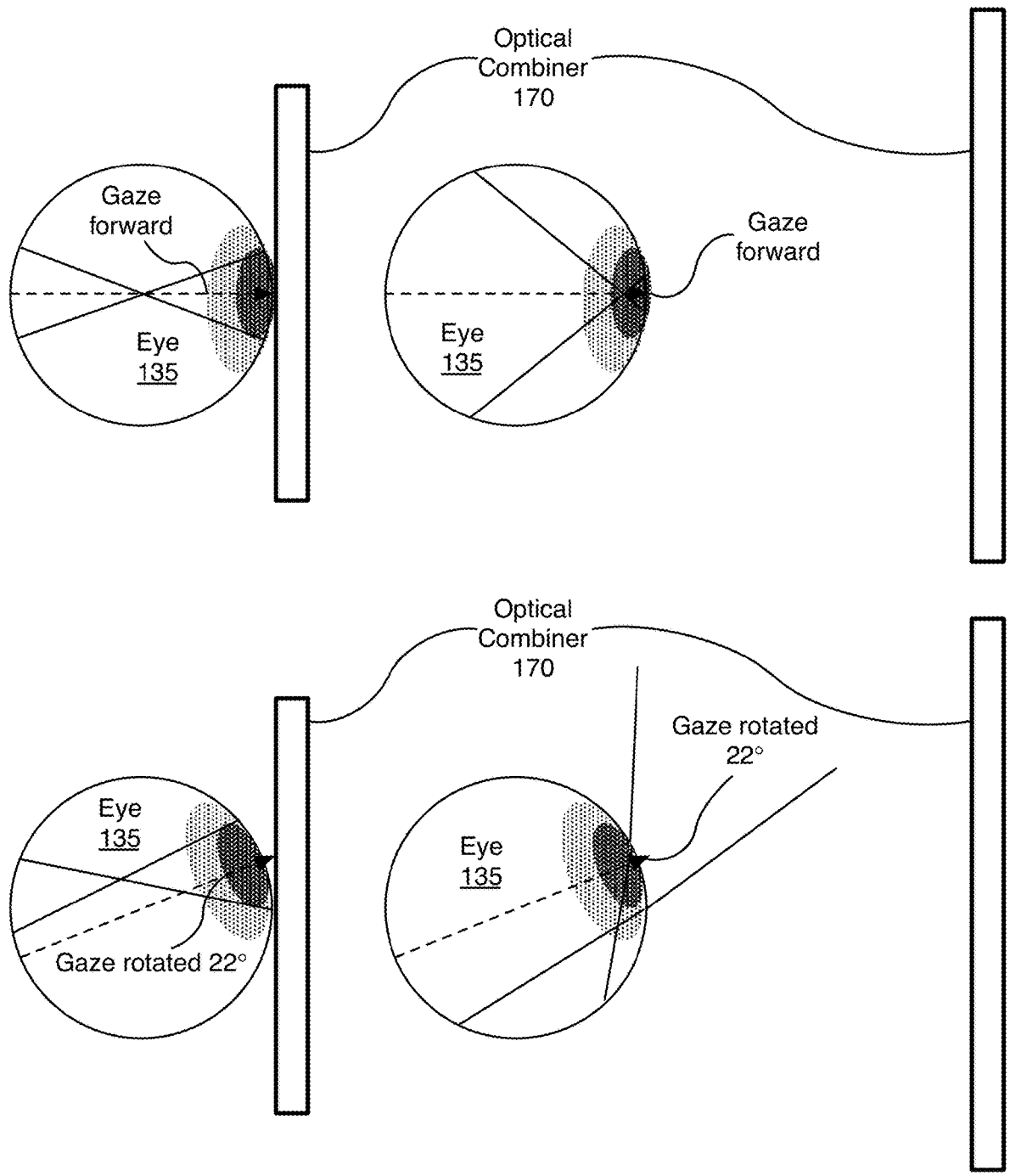
FIG. 2A illustrates the field of view for different nodal points and gaze directions, in accordance with one embodiment.

FIG. 2A illustrates the field of view for different nodal points and gaze directions, in accordance with one embodiment. While placing the focus of the optical combiner 170 at the pupil of the eye 135 has obvious advantages in terms of FOV, for a given location of the light engine 132, that advantage is lost if the user changes her gaze direction. FIG. 2A shows the same displacements of the optical combiner 170 from the eye 135 for two situations: the gaze forward and the gaze inclined by 22°. The top row shows the results for when the gaze is forward. The bottom row shows the results for when the gaze is inclined by 22°.

Figure 2B:
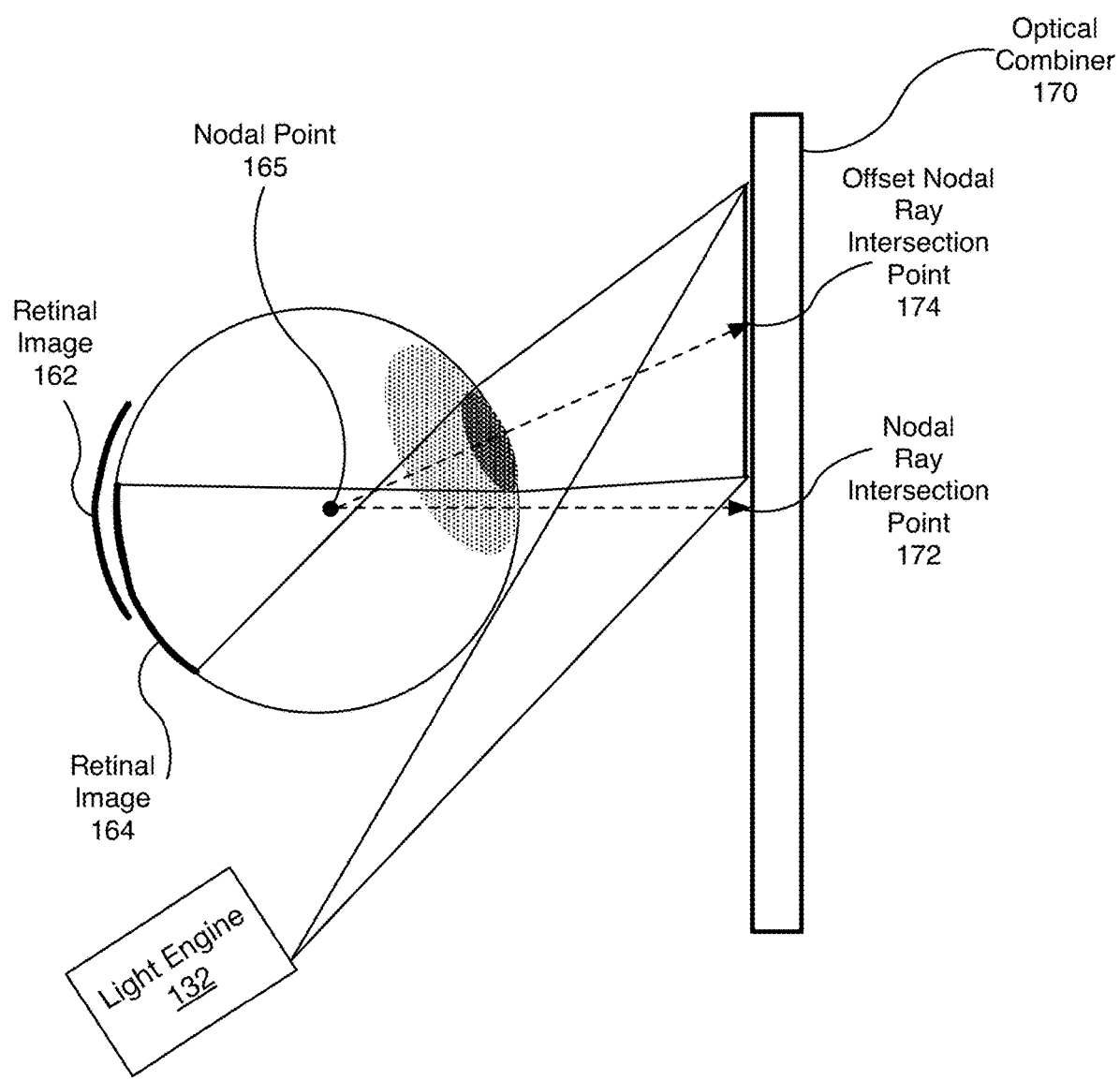
FIG. 2B illustrates the portion of the display system of FIG. 1B for creating converging rays for the eye using a different nodal ray intersection point compared with the portion of the optical combiner system shown in FIG. 1D, in accordance with one embodiment.

The dotted line denotes the optical axis of the eye 135. The illustrated optical axis passes through the center of the pupil and the rotational center of the eye 135, intersecting the retina. Note that when the gaze is directed forward, the refracted rays cross the optical axis of the eye 135 and the limiting rays intersect the retina equidistant from where the optical axis intersects the retina. The retinal image generated by the light diffracted by the optical combiner 170, then, should be centered within the retina. Note that, as shown in the second row, the retinal image is not centered on the retina when the gaze is rotated counter-clockwise by 22°. When the light rays are directed towards the rotational center 105 of the eye 135, as shown in FIG. 1D, the rotation of the eye 135 about its geometrical center preserves the symmetry of the light rays entering the eye 135 and the retinal image resulting from the light rays that are redirected by the optical combiner 160 is always centered on the retina (as shown in FIG. 2B). The symmetry of the angles with which the light rays enter the eye 135 not preserved if the optical combiner 160 does not redirect the light rays to converge at the rotational center 105 of the eye 135.

Specifically, as shown in the (left side) examples, with the optical combiner 170 very close to the eye 135 in FIG. 2A, the retinal image shifts from the center of the retina to "float" upward when the gaze shifts from the forward position to be rotated 22°. Note that the light rays, after being refracted within the eye 135, cross at the rotational center 105 of the eye 135 while the gaze is forward and produce a retinal image centered on the retina. In contrast, in the configuration shown in FIG. 1D, the optical combiner 160 redirects the light rays towards the rotational center 105 of the eye 135, but the crossing of the limiting rays, after being refracted within the eye 135, is actually in front of the rotational center 105 of the eye 135. As shown in FIG. 2A, when the gaze is rotated 22°, the retinal image "floats" upward and is no longer centered on the retina. The shifting of the retinal image on the retina as the gaze direction changes combined with the small FOV are disadvantages. Therefore, having the redirected and then refracted light rays cross at the rotational center 105 of the eye 135 may not be the best configuration.

In another example, the optical combiner 170 is positioned further from the eye 135 to increase the FOV. As shown in FIG. 2A, the refracted light rays cross near the pupil and the angles over which the viewer can change her/his gaze are limited. The distance between the eye 135 and the optical combiner 170 is chosen such that, when the viewer is gazing forward, the viewer's FOV is limited only by the width of the optical combiner 170. If the viewer rotates his/her gaze by 22°, then most of the light rays from the optical combiner 170 (assuming a fixed position of the light engine 132) no longer enter the pupil—making it impossible to perceive an image from the optical combiner 170. If the optical combiner 170 were infinitely wide, light rays redirected by the optical combiner 170 could be directed into the pupil; but the retinal image would float away from the center of the retina.

Rather than redirecting the light rays to cross at the rotational center 105 of the eye 135, as shown in FIG. 1D, the optical combiner 170 is positioned further from the eye 135 than the configuration on the left side of FIG. 2A. In FIG. 1D, the light rays are redirected to converge towards the rotational center 105 of the eye 235. Therefore, the FOV is reduced compared with the configuration of the right side of FIG. 2A and the resulting retinal image may be used to generate the foveal portion of a display. A different mechanism may be used to generate the peripheral portion of the display. A high-resolution image may be projected onto the optical combiner 170 by the light engine 132. This high-resolution image may consume all the area of the optical combiner 170 or the high-resolution image may be a smaller image (i.e., a foveal image) that is just larger than the user's FOV (for the optical combiner 170) and centered in the direction in which the user is gazing.

FIG. 2B illustrates the portion of the display system 145 of FIG. 1B for creating converging rays for the eye 135 using a different nodal ray intersection point compared with the portion of the display system 145 shown in FIG. 1D, in accordance with one embodiment. The nodal ray intersection point 172 corresponds with a forward gaze of the user and a nodal ray intersection point 174 corresponds with a gaze of the user that is offset to the left (the diagram is a top-down view). A retinal image 164 is produced by the redirected light rays according to the region of the optical combiner 170 centered at the offset nodal ray intersection point 174. The optical combiner 170 redirects the light rays generated by the light engine 132 to converge towards the nodal point 165 that is located at the rotational center 105 of the eye 135.

In one embodiment, an origin of the light rays generated by the light engine 132 is offset responsive to changes in the gaze direction so that the foveal image is centered about the user's gaze direction. As shown in FIG. 2B, the origin of the light rays generated by the light engine 132 are offset to the right compared with an origin of the light rays generated by the light engine 132 shown in FIG. 1D. In one embodiment, the light engine 132 comprises a number of projectors that equals the number of nodal ray intersection points, with each projector dedicated to either the same nodal point within the eye 135 or a different nodal points within the eye 135.

In one embodiment, the offset comprises a lateral shift. The position of the light engine 132 may be shifted mechanically or optically. In another embodiment, the light engine 132 includes two or more projectors that are laterally offset relative to each other and one projector is selected at a time to generate the light rays. In other words, the projectors are time-multiplexed to generate the retinal images 162 and 164. The one projector that is selected during any particular time is selected based on the user's gaze direction.

Additionally, the bandwidth of the Bragg matching condition may be employed to laterally shift or offset an origin of the light rays generated by the light engine 132 to shift the nodal ray intersection point 172 to the offset nodal ray intersection point 174 based on the viewer's gaze. The Bragg matching condition is defined for one given angle of the reference beam in holography. Bragg matching may be used with a single layer of the optical combiner 170 and a single projector by physically or optically shifting the origin of the light rays. Bragg matching may be used alone or in combination with the optical combiner 170, when the optical combiner 170 is configured to have two or more responses, to provide multiple offset origins of the light rays corresponding to multiple nodal ray intersection points.

In one embodiment, an optical combiner 170 is a HOE having at least two responses, where a first response directs the light rays intersecting the optical combiner 170 at a first range of locations to the nodal point 168 and a second response directs the light rays intersecting the optical combiner 170 at a second range of locations to the nodal point 168. A response may be configured within either a dedicated layer of a multi-layer HOE or a dedicated portion of a single layer HOE. In one embodiment, each response corresponds with a different nodal ray intersection point and gaze direction.

A depth of field effect may be achieved (independent of rendering) by producing retinal images having different nodal ray intersection points, such as the retinal images 162 and 164 associated with the nodal ray intersection point 172 and the offset nodal ray intersection point 174, respectively. Several techniques may be used to generate two or more images having different nodal ray intersection points. As previously described, an HOE having at least two responses may be used, where each response corresponds with a different nodal ray intersection point. The light engine 132 may employ either time multiplexing or a separate projector for each nodal ray intersection point to generate the images. In one embodiment, a depth of field effect is produced by generating images centered around at least two ray intersection points on the optical combiner 170 that are spaced less than 8 mm apart. The images appear to the viewer to be at different depths.

Increased color resolution and gamut may be achieved by producing per-color channel (e.g., red, green, blue) images, each having a different nodal ray intersection point. The optical combiner 170 may include an HOE that is written to have a different response for each color channel wavelength. For example, a first response may redirect light rays of a pre-determined wavelength range that is associated with a first color channel and a second response may redirect light rays of a pre-determined wavelength range that is associated with a second color channel. As previously described, the optical combiner 170 may have at least two responses, where each response corresponds with a different nodal ray intersection point and a different color channel wavelength. The light engine 132 may employ either time multiplexing or a separate projector for each nodal ray intersection point and wavelength to generate the per-color channel images.

For example, red, green, and blue color channels are associated with a first, second, and third nodal ray intersection point, respectively. The optical combiner 170 redirects light rays for the different color channels to converge at respective nodal points.

Figure 2C:
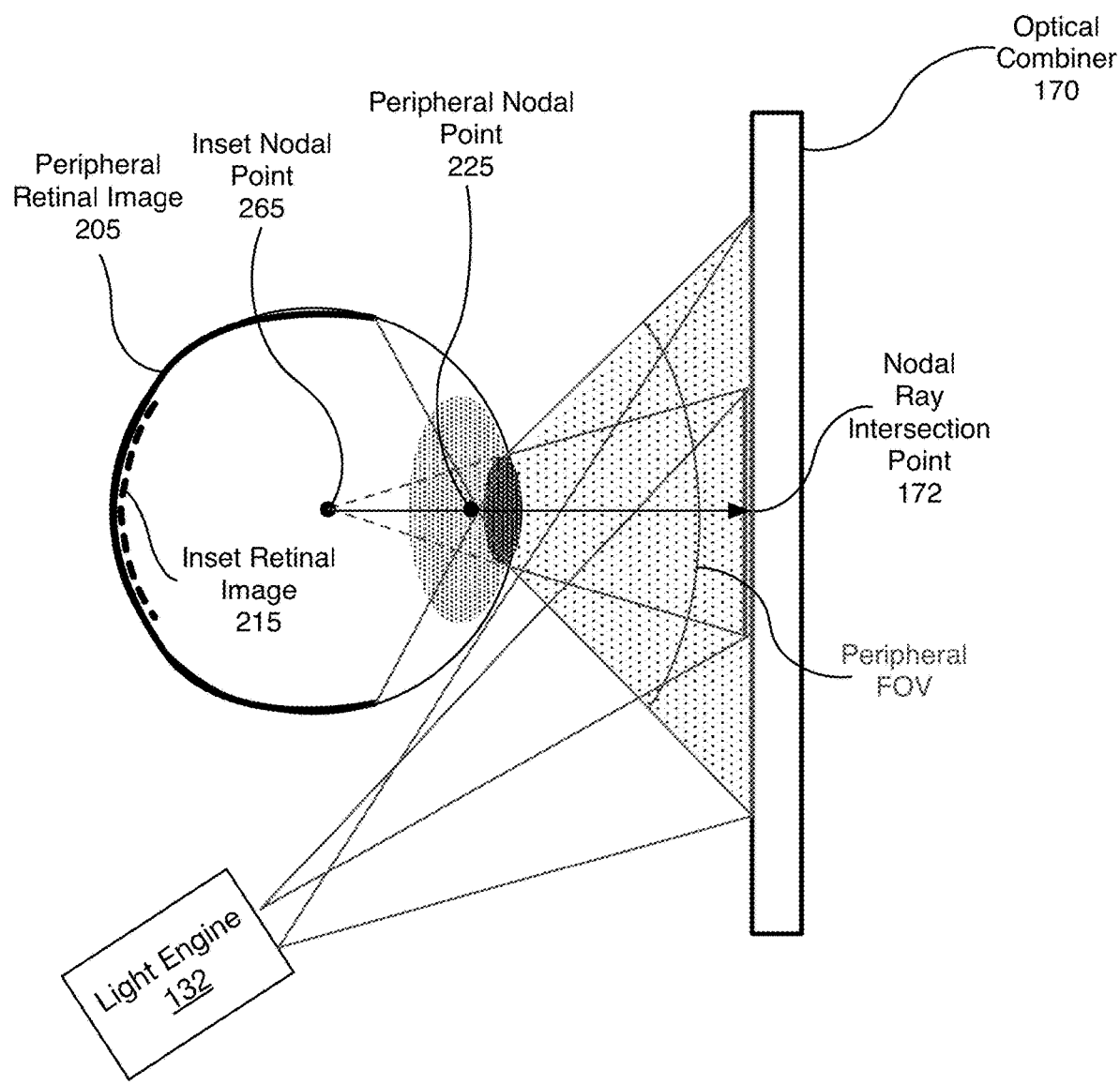
FIG. 2C illustrates the portion of the display system of FIG. 1B for creating converging rays for the eye for two different FOVs, in accordance with one embodiment.

FIG. 2C illustrates the portion of the display system 145 of FIG. 1B for creating converging rays for the eye 135 for two different FOVs, in accordance with one embodiment. The light engine 132 generates an inset foveal image and a peripheral image that are both centered at the nodal ray intersection point 172 on the optical combiner 170. The optical combiner 170 redirects the light rays for the inset foveal image to converge towards the inset nodal point 265. In one embodiment, the inset nodal point is located at the rotational center 105 of the eye 135. The optical combiner 170 redirects the light rays for the peripheral image to converge towards the peripheral nodal point 225. The redirected light rays for the inset foveal image produce the inset retinal image 215 and the redirected light rays for the peripheral image produce the peripheral retinal image 205. A depth of field effect may be achieved (independent of rendering) by producing retinal images with light rays redirected to two different nodal points, such as the nodal points 265 and 225. In one embodiment, the light rays for the peripheral image are also redirected to converge towards the inset nodal point 265. In one embodiment, the peripheral retinal image 205 may be rendered to appear at a different depth compared with the inset retinal image 215.

In one embodiment, the inset retinal image 215 is centered within cutout portion of the peripheral retinal image 205. In one embodiment, the inset retinal image 215 is centered within the peripheral retinal image 205. As shown in FIG. 2C, a peripheral FOV in a shaded region between the pupil and the optical combiner 170 is larger compared with a FOV of the inset foveal image. The entire FOV corresponding to the inset retinal image 205 is within the peripheral FOV.

The light engine 132 may be a single projector that time-multiplexes between outputting the inset foveal image and the peripheral image, such that the inset foveal image is associated with one response of the optical combiner 170 and the peripheral image is associated with another response of the optical combiner 170 (i.e., by varying the wavelength, nodal ray intersection point, or phase).

Figure 2D:
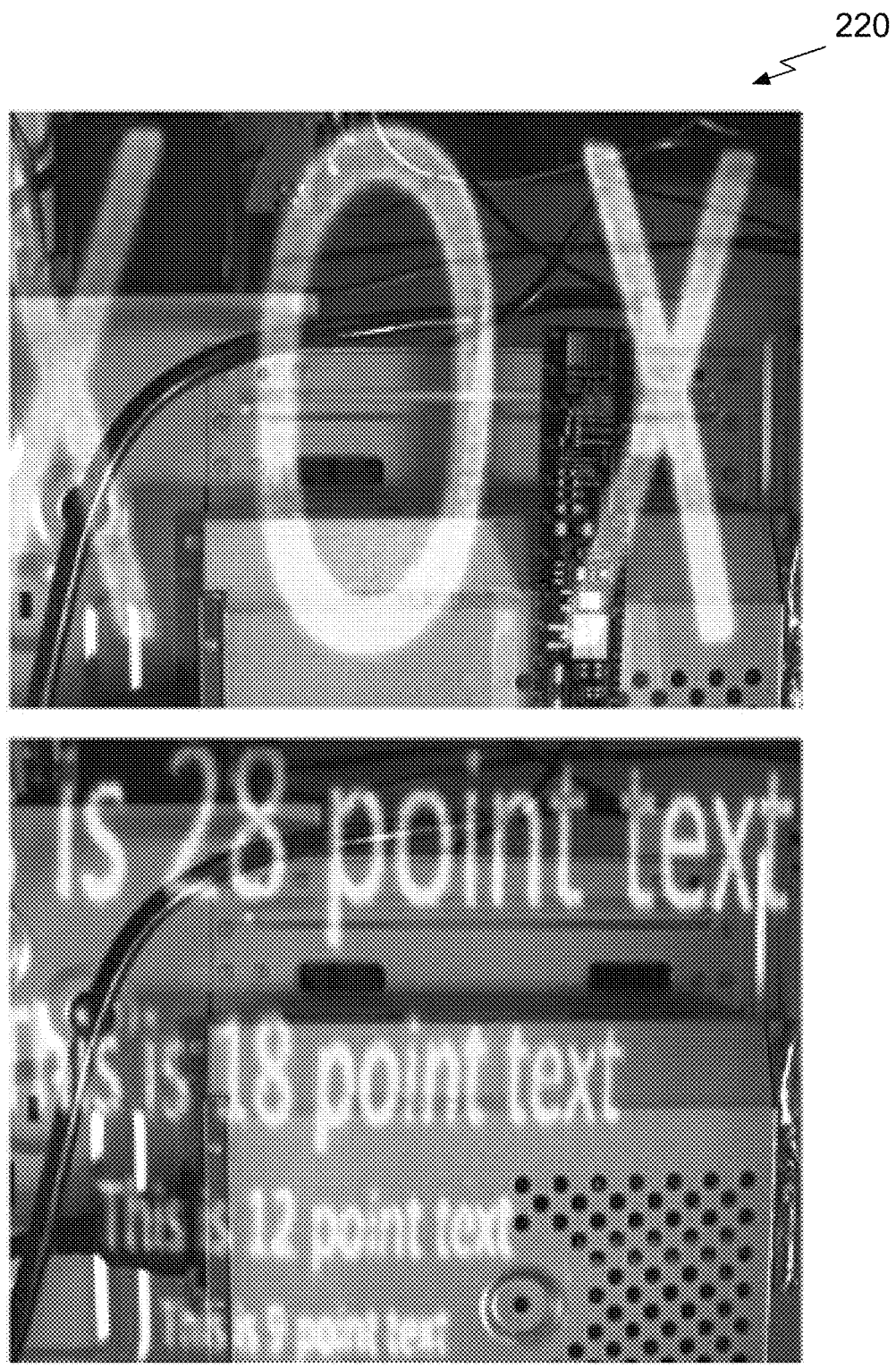
FIG. 2D illustrates images projected onto an optical combiner for an AR device, in accordance with one embodiment.

FIG. 2D illustrates images 220 projected onto the optical combiner 170 for an AR device, in accordance with one embodiment. In one embodiment, the optical combiner 170 is an HOE. An advantage of HOEs, is that the HOE becomes nearly transparent to light rays that are different in terms of wavelength or propagation direction compared with the reference beam and object beam. Therefore, an HOE may be used to create the desired illumination in AR devices without occluding a view of the environment. The overall configuration of the display system 145 is also well-suited for light-weight and compact AR devices because only a single HOE 150, optical combiner 160, or optical combiner 170 is needed for each eye 135.

The images 220 comprise text that is projected onto the HOE 150 and redirected to produce retinal images. The top image is of a pattern of 72-point X's and O's. The bottom image is of green text with decreasing text size (28 pt., 18 pt., 12 pt., and 9 pt.). FIG. 2D illustrates what the user sees when looking through the HOE 150, where the background (behind the green lettering) is equipment in the environment. Note that light from the environment transverses the HOE 150 without being effected. The light from the image projected onto the HOE 150 is simply added to the environment that the user would normally see.

Traditionally holographic combiners have been programmed to function as mirrors for liquid crystal displays in HMD designs. Because the traditional uses of holographic combiners do not take advantage of retinal imaging, the holographic elements were positioned inches away from the surface of the user's eye—thus, creating HMDs that are quite bulky. Other efforts have tried using holographic waveguides—waveguides that use holograms to couple light into and out of the waveguide. Solutions that use only one waveguide have been difficult to design and tend to suffer from significant color dispersion, cross talk between the different color channels, and "ghost images." Multiple waveguides may be used to physically separate the different color channels to avoid problematic interactions. However, multiple waveguides increases the bulk, complexity, and alignment difficulties for the system. Curved holographic combiners that holographically encode an array of microlenses accomplish a near-eye configuration; however, the user of an HMD that uses these optical combiners also has to wear specially designed contact lenses. The requirement of wearing special contact lenses presents a significant barrier to using the system both in terms of the complexity of the steps that the user would need to perform to use the system and in terms of the cost of the system.

Importantly, the display system 145 may be implemented using the HOEs 150, as shown, or using optical combiners 160 or 170 in place of the HOEs 150 to produce an inset foveal image that is combined with a peripheral image. The display system 145 does not suffer from issues of chromatic dispersion or ghost images. There is no need for the user to wear contact lenses to see images with the display system 145. The inset foveal image and the peripheral image are both redirected by the HOEs 150 or optical combiners 160 or 170 to generate the retinal image and the peripheral image. The HOE 150 or optical combiners 160 and 170 may be configured to support multiple nodal ray intersection points, where each nodal ray intersection point corresponds to a different gaze direction. Alternatively, the different nodal ray intersection points may correspond to different image depths or different wavelengths.

Parallel Processing Architecture

Figure 3:
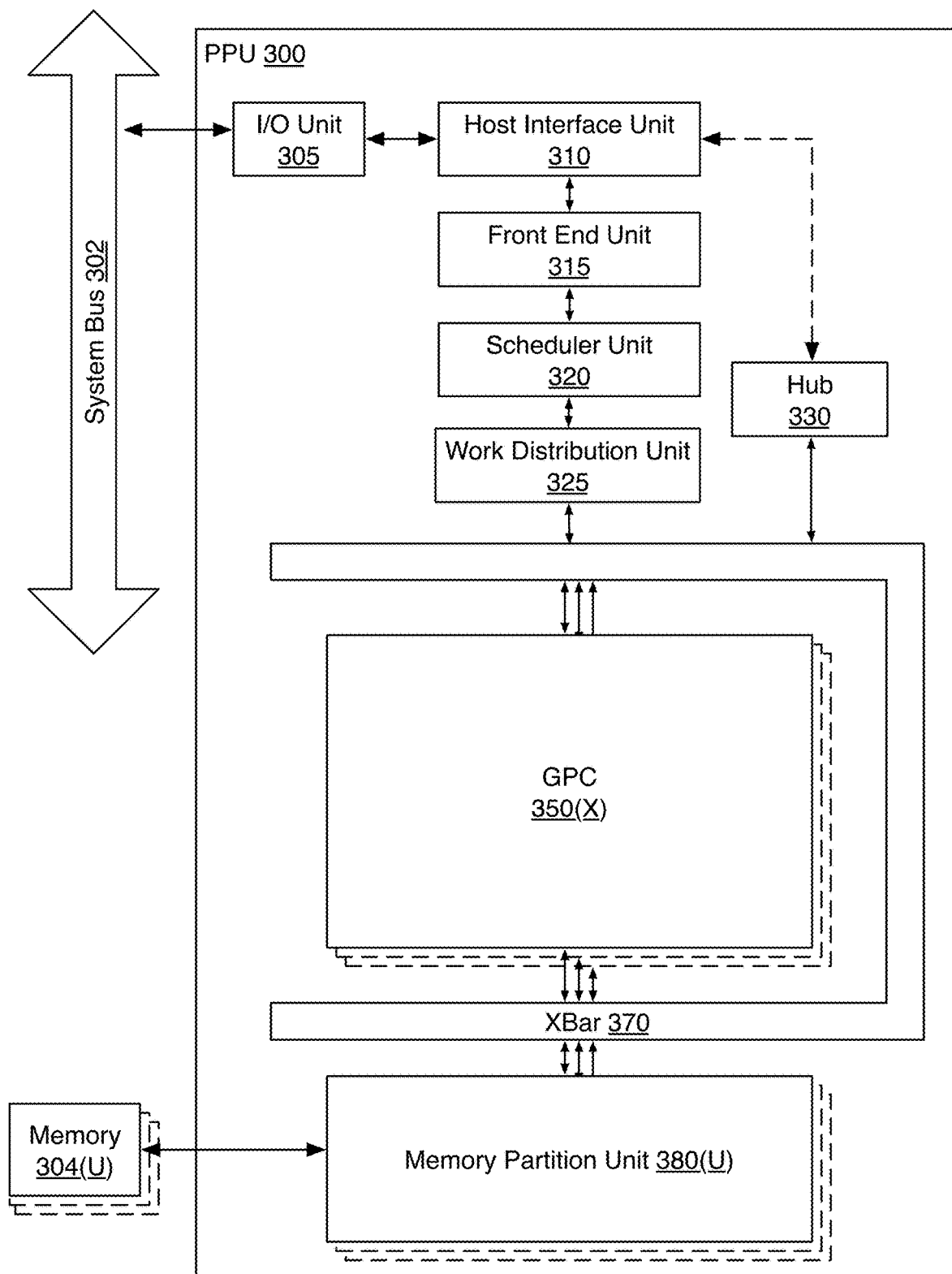
FIG. 3 illustrates a parallel processing unit, in accordance with one embodiment.

FIG. 3 illustrates a parallel processing unit (PPU) 300, in accordance with one embodiment. In one embodiment, the PPU 300 is a multi-threaded processor that is implemented on one or more integrated circuit devices. The PPU 300 is a latency hiding architecture designed to process many threads in parallel. A thread (i.e., a thread of execution) is an instantiation of a set of instructions configured to be executed by the PPU 300. In one embodiment, the PPU 300 is a graphics processing unit (GPU) configured to implement a graphics rendering pipeline for processing three-dimensional (3D) graphics data in order to generate two-dimensional (2D) image data for display on a display device such as a liquid crystal display (LCD) device. In other embodiments, the PPU 300 may be utilized for performing general-purpose computations. While one exemplary parallel processor is provided herein for illustrative purposes, it should be strongly noted that such processor is set forth for illustrative purposes only, and that any processor may be employed to supplement and/or substitute for the same.

As shown in FIG. 3, the PPU 300 includes an Input/Output (I/O) unit 305, a host interface unit 310, a front end unit 315, a scheduler unit 320, a work distribution unit 325, a hub 330, a crossbar (Xbar) 370, one or more general processing clusters (GPCs) 350, and one or more partition units 380. The PPU 300 may be connected to a host processor or other peripheral devices via a system bus 302. The PPU 300 may also be connected to a local memory comprising a number of memory devices 304. In one embodiment, the local memory may comprise a number of dynamic random access memory (DRAM) devices.

The I/O unit 305 is configured to transmit and receive communications (i.e., commands, data, etc.) from a host processor (not shown) over the system bus 302. The I/O unit 305 may communicate with the host processor directly via the system bus 302 or through one or more intermediate devices such as a memory bridge. In one embodiment, the I/O unit 305 implements a Peripheral Component Interconnect Express (PCIe) interface for communications over a PCIe bus. In alternative embodiments, the I/O unit 305 may implement other types of well-known interfaces for communicating with external devices.

The I/O unit 305 is coupled to a host interface unit 310 that decodes packets received via the system bus 302. In one embodiment, the packets represent commands configured to cause the PPU 300 to perform various operations. The host interface unit 310 transmits the decoded commands to various other units of the PPU 300 as the commands may specify. For example, some commands may be transmitted to the front end unit 315. Other commands may be transmitted to the hub 330 or other units of the PPU 300 such as one or more copy engines, a video encoder, a video decoder, a power management unit, etc. (not explicitly shown). In other words, the host interface unit 310 is configured to route communications between and among the various logical units of the PPU 300.

In one embodiment, a program executed by the host processor encodes a command stream in a buffer that provides workloads to the PPU 300 for processing. A workload may comprise several instructions and data to be processed by those instructions. The buffer is a region in a memory that is accessible (i.e., read/write) by both the host processor and the PPU 300. For example, the host interface unit 310 may be configured to access the buffer in a system memory connected to the system bus 302 via memory requests transmitted over the system bus 302 by the I/O unit 305. In one embodiment, the host processor writes the command stream to the buffer and then transmits a pointer to the start of the command stream to the PPU 300. The host interface unit 310 provides the front end unit 315 with pointers to one or more command streams. The front end unit 315 manages the one or more streams, reading commands from the streams and forwarding commands to the various units of the PPU 300.

The front end unit 315 is coupled to a scheduler unit 320 that configures the various GPCs 350 to process tasks defined by the one or more streams. The scheduler unit 320 is configured to track state information related to the various tasks managed by the scheduler unit 320. The state may indicate which GPC 350 a task is assigned to, whether the task is active or inactive, a priority level associated with the task, and so forth. The scheduler unit 320 manages the execution of a plurality of tasks on the one or more GPCs 350.

The scheduler unit 320 is coupled to a work distribution unit 325 that is configured to dispatch tasks for execution on the GPCs 350. The work distribution unit 325 may track a number of scheduled tasks received from the scheduler unit 320. In one embodiment, the work distribution unit 325 manages a pending task pool and an active task pool for each of the GPCs 350. The pending task pool may comprise a number of slots (e.g., 32 slots) that contain tasks assigned to be processed by a particular GPC 350. The active task pool may comprise a number of slots (e.g., 4 slots) for tasks that are actively being processed by the GPCs 350. As a GPC 350 finishes the execution of a task, that task is evicted from the active task pool for the GPC 350 and one of the other tasks from the pending task pool is selected and scheduled for execution on the GPC 350. If an active task has been idle on the GPC 350, such as while waiting for a data dependency to be resolved, then the active task may be evicted from the GPC 350 and returned to the pending task pool while another task in the pending task pool is selected and scheduled for execution on the GPC 350.

The work distribution unit 325 communicates with the one or more GPCs 350 via XBar 370. The XBar 370 is an interconnect network that couples many of the units of the PPU 300 to other units of the PPU 300. For example, the XBar 370 may be configured to couple the work distribution unit 325 to a particular GPC 350. Although not shown explicitly, one or more other units of the PPU 300 are coupled to the host interface unit 310. The other units may also be connected to the XBar 370 via a hub 330.

The tasks are managed by the scheduler unit 320 and dispatched to a GPC 350 by the work distribution unit 325. The GPC 350 is configured to process the task and generate results. The results may be consumed by other tasks within the GPC 350, routed to a different GPC 350 via the XBar 370, or stored in the memory 304. The results can be written to the memory 304 via the partition units 380, which implement a memory interface for reading and writing data to/from the memory 304. In one embodiment, the PPU 300 includes a number U of partition units 380 that is equal to the number of separate and distinct memory devices 304 coupled to the PPU 300. A partition unit 380 will be described in more detail below in conjunction with FIG. 4B.

In one embodiment, a host processor executes a driver kernel that implements an application programming interface (API) that enables one or more applications executing on the host processor to schedule operations for execution on the PPU 300. An application may generate instructions (i.e., API calls) that cause the driver kernel to generate one or more tasks for execution by the PPU 300. The driver kernel outputs tasks to one or more streams being processed by the PPU 300. Each task may comprise one or more groups of related threads, referred to herein as a warp. A thread block may refer to a plurality of groups of threads including instructions to perform the task. Threads in the same group of threads may exchange data through shared memory. In one embodiment, a group of threads comprises 32 related threads.

Figure 4A:
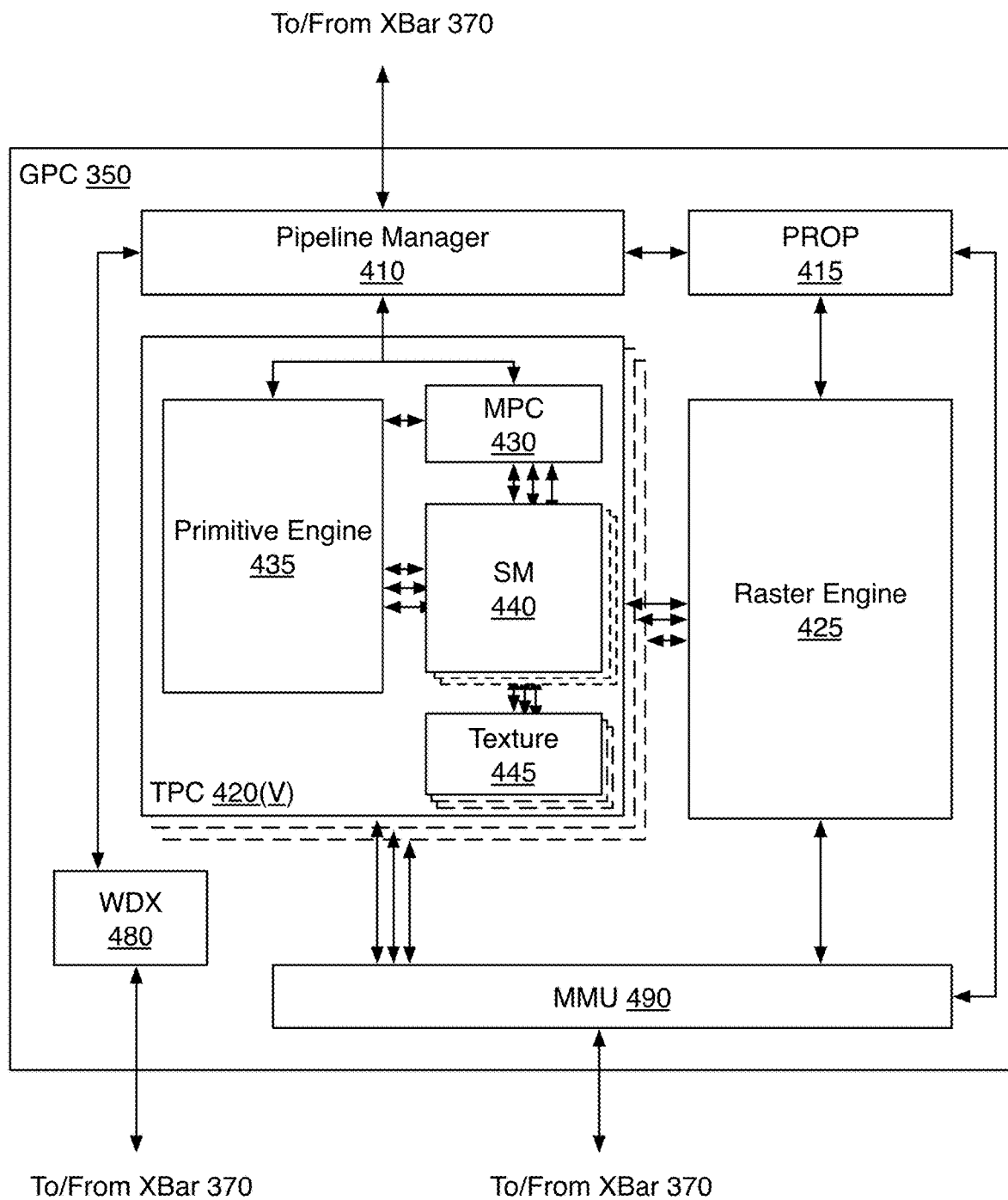
FIG. 4A illustrates a general processing cluster within the parallel processing unit of FIG. 3, in accordance with one embodiment.

FIG. 4A illustrates a GPC 350 within the PPU 300 of FIG. 3, in accordance with one embodiment. As shown in FIG. 4A, each GPC 350 includes a number of hardware units for processing tasks. In one embodiment, each GPC 350 includes a pipeline manager 410, a pre-raster operations unit (PROP) 415, a raster engine 425, a work distribution crossbar (WDX) 480, a memory management unit (MMU) 490, and one or more Texture Processing Clusters (TPCs) 420. It will be appreciated that the GPC 350 of FIG. 4A may include other hardware units in lieu of or in addition to the units shown in FIG. 4A.

In one embodiment, the operation of the GPC 350 is controlled by the pipeline manager 410. The pipeline manager 410 manages the configuration of the one or more TPCs 420 for processing tasks allocated to the GPC 350. In one embodiment, the pipeline manager 410 may configure at least one of the one or more TPCs 420 to implement at least a portion of a graphics rendering pipeline. For example, a TPC 420 may be configured to execute a vertex shader program on the programmable streaming multiprocessor (SM) 440. The pipeline manager 410 may also be configured to route packets received from the work distribution unit 325 to the appropriate logical units within the GPC 350. For example, some packets may be routed to fixed function hardware units in the PROP 415 and/or raster engine 425 while other packets may be routed to the TPCs 420 for processing by the primitive engine 435 or the SM 440.

The PROP unit 415 is configured to route data generated by the raster engine 425 and the TPCs 420 to a Raster Operations (ROP) unit in the partition unit 380, described in more detail below. The PROP unit 415 may also be configured to perform optimizations for color blending, organize pixel data, perform address translations, and the like.

The raster engine 425 includes a number of fixed function hardware units configured to perform various raster operations. In one embodiment, the raster engine 425 includes a setup engine, a coarse raster engine, a culling engine, a clipping engine, a fine raster engine, and a tile coalescing engine. The setup engine receives transformed vertices and generates plane equations associated with the geometric primitive defined by the vertices. The plane equations are transmitted to the coarse raster engine to generate coverage information (e.g., an x,y coverage mask for a tile) for the primitive. The output of the coarse raster engine may be transmitted to the culling engine where fragments associated with the primitive that fail a z-test are culled, and transmitted to a clipping engine where fragments lying outside a viewing frustum are clipped. Those fragments that survive clipping and culling may be passed to a fine raster engine to generate attributes for the pixel fragments based on the plane equations generated by the setup engine. The output of the raster engine 425 comprises fragments to be processed, for example, by a fragment shader implemented within a TPC 420.

Each TPC 420 included in the GPC 350 includes an M-Pipe Controller (MPC) 430, a primitive engine 435, one or more SMs 440, and one or more texture units 445. The MPC 430 controls the operation of the TPC 420, routing packets received from the pipeline manager 410 to the appropriate units in the TPC 420. For example, packets associated with a vertex may be routed to the primitive engine 435, which is configured to fetch vertex attributes associated with the vertex from the memory 304. In contrast, packets associated with a shader program may be transmitted to the SM 440.

In one embodiment, the texture units 445 are configured to load texture maps (e.g., a 2D array of texels) from the memory 304 and sample the texture maps to produce sampled texture values for use in shader programs executed by the SM 440. The texture units 445 implement texture operations such as filtering operations using mip-maps (i.e., texture maps of varying levels of detail). The texture unit 445 is also used as the Load/Store path for SM 440 to MMU 490. In one embodiment, each TPC 420 includes two (2) texture units 445.

The SM 440 comprises a programmable streaming processor that is configured to process tasks represented by a number of threads. Each SM 440 is multi-threaded and configured to execute a plurality of threads (e.g., 32 threads) from a particular group of threads concurrently. In one embodiment, the SM 440 implements a SIMD (Single-Instruction, Multiple-Data) architecture where each thread in a group of threads (i.e., a warp) is configured to process a different set of data based on the same set of instructions. All threads in the group of threads execute the same instructions. In another embodiment, the SM 440 implements a SIMT (Single-Instruction, Multiple Thread) architecture where each thread in a group of threads is configured to process a different set of data based on the same set of instructions, but where individual threads in the group of threads are allowed to diverge during execution. In other words, when an instruction for the group of threads is dispatched for execution, some threads in the group of threads may be active, thereby executing the instruction, while other threads in the group of threads may be inactive, thereby performing a no-operation (NOP) instead of executing the instruction. The SM 440 is described in more detail below in conjunction with FIG. 5.

The MMU 490 provides an interface between the GPC 350 and the partition unit 380. The MMU 490 may provide translation of virtual addresses into physical addresses, memory protection, and arbitration of memory requests. In one embodiment, the MMU 490 provides one or more translation lookaside buffers (TLBs) for performing translation of virtual addresses into physical addresses in the memory 304.

Figure 4B:
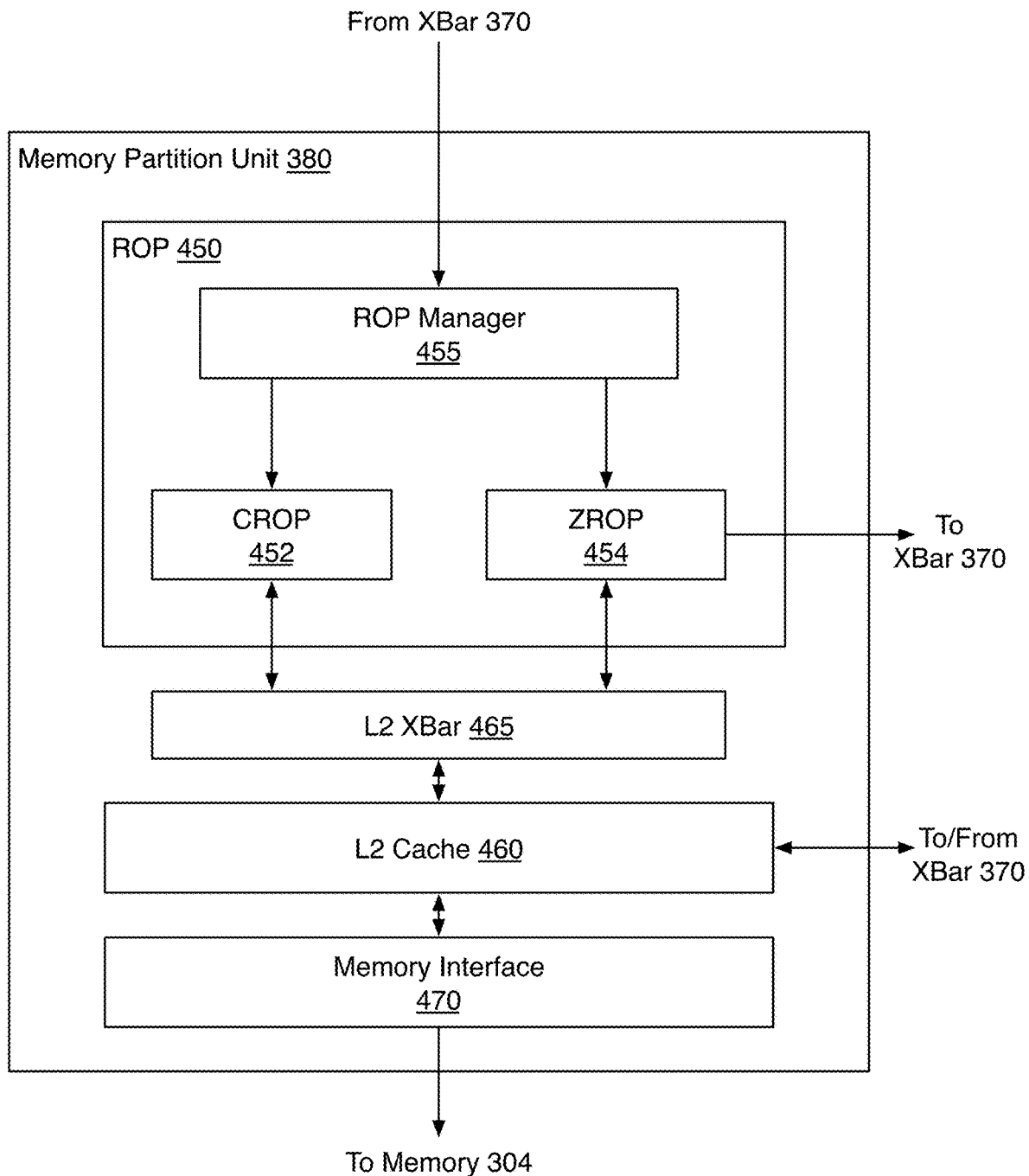
FIG. 4B illustrates a memory partition unit of the parallel processing unit of FIG. 3, in accordance with one embodiment.

FIG. 4B illustrates a memory partition unit 380 of the PPU 300 of FIG. 3, in accordance with one embodiment. As shown in FIG. 4B, the memory partition unit 380 includes a Raster Operations (ROP) unit 450, a level two (L2) cache 460, a memory interface 470, and an L2 crossbar (XBar) 465. The memory interface 470 is coupled to the memory 304. Memory interface 470 may implement 16, 32, 64, 128-bit data buses, or the like, for high-speed data transfer. In one embodiment, the PPU 300 incorporates U memory interfaces 470, one memory interface 470 per partition unit 380, where each partition unit 380 is connected to a corresponding memory device 304. For example, PPU 300 may be connected to up to U memory devices 304, such as graphics double-data-rate, version 5, synchronous dynamic random access memory (GDDR5 SDRAM). In one embodiment, the memory interface 470 implements a DRAM interface and U is equal to 8.

In one embodiment, the PPU 300 implements a multi-level memory hierarchy. The memory 304 is located off-chip in SDRAM coupled to the PPU 300. Data from the memory 304 may be fetched and stored in the L2 cache 460, which is located on-chip and is shared between the various GPCs 350. As shown, each partition unit 380 includes a portion of the L2 cache 460 associated with a corresponding memory device 304. Lower level caches may then be implemented in various units within the GPCs 350. For example, each of the SMs 440 may implement a level one (L1) cache. The L1 cache is private memory that is dedicated to a particular SM 440. Data from the L2 cache 460 may be fetched and stored in each of the L1 caches for processing in the functional units of the SMs 440. The L2 cache 460 is coupled to the memory interface 470 and the XBar 370.

The ROP unit 450 includes a ROP Manager 455, a Color ROP (CROP) unit 452, and a Z ROP (ZROP) unit 454. The CROP unit 452 performs raster operations related to pixel color, such as color compression, pixel blending, and the like. The ZROP unit 454 implements depth testing in conjunction with the raster engine 425. The ZROP unit 454 receives a depth for a sample location associated with a pixel fragment from the culling engine of the raster engine 425. The ZROP unit 454 tests the depth against a corresponding depth in a depth buffer for a sample location associated with the fragment. If the fragment passes the depth test for the sample location, then the ZROP unit 454 updates the depth buffer and transmits a result of the depth test to the raster engine 425. The ROP Manager 455 controls the operation of the ROP unit 450. It will be appreciated that the number of partition units 380 may be different than the number of GPCs 350 and, therefore, each ROP unit 450 may be coupled to each of the GPCs 350. Therefore, the ROP Manager 455 tracks packets received from the different GPCs 350 and determines which GPC 350 that a result generated by the ROP unit 450 is routed to. The CROP unit 452 and the ZROP unit 454 are coupled to the L2 cache 460 via an L2 XBar 465.

Figure 5:
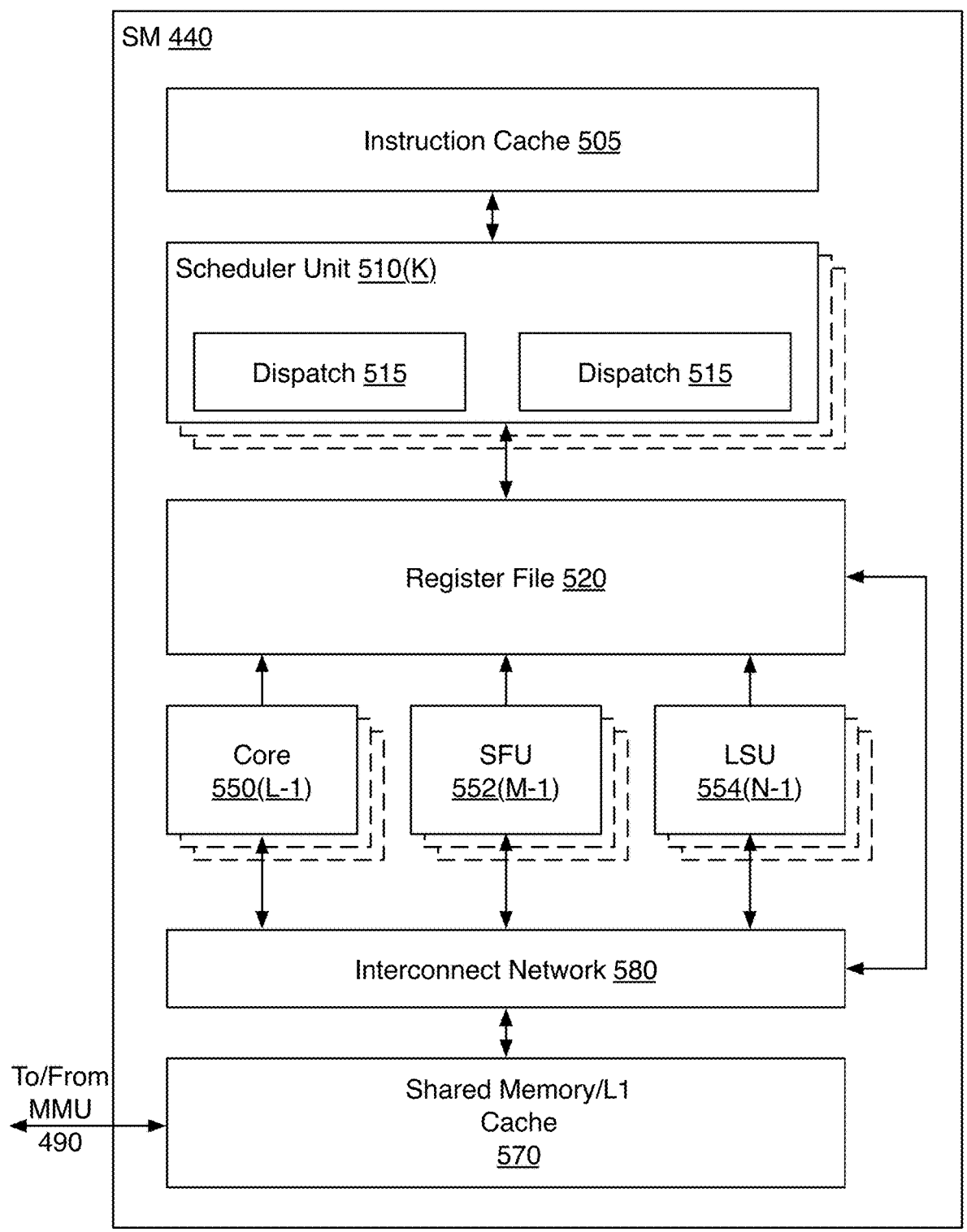
FIG. 5 illustrates the streaming multi-processor of FIG. 4A, in accordance with one embodiment.

FIG. 5 illustrates the streaming multi-processor 440 of FIG. 4A, in accordance with one embodiment. As shown in FIG. 5, the SM 440 includes an instruction cache 505, one or more scheduler units 510, a register file 520, one or more processing cores 550, one or more special function units (SFUs) 552, one or more load/store units (LSUs) 554, an interconnect network 580, a shared memory/L1 cache 570. In one embodiment, the instruction cache 105, the load/store unit 154, and the register file 115, shown in FIG. 1B is the instruction cache 505, the load/store unit (LSU) 554, and the register file 520, respectively.

As described above, the work distribution unit 325 dispatches tasks for execution on the GPCs 350 of the PPU 300. The tasks are allocated to a particular TPC 420 within a GPC 350 and, if the task is associated with a shader program, the task may be allocated to an SM 440. The scheduler unit 510 receives the tasks from the work distribution unit 325 and manages instruction scheduling for one or more groups of threads (i.e., warps) assigned to the SM 440. The scheduler unit 510 schedules threads for execution in groups of parallel threads, where each group is called a warp. In one embodiment, each warp includes 32 threads. The scheduler unit 510 may manage a plurality of different warps, scheduling the warps for execution and then dispatching instructions from the plurality of different warps to the various functional units (i.e., cores 550, SFUs 552, and LSUs 554) during each clock cycle.

Each dispatch unit 515 is configured to transmit instructions to one or more of the functional units. In the embodiment shown in FIG. 5, the scheduler unit 510 includes two dispatch units 515 that enable two different instructions from the same warp to be dispatched during each clock cycle. In alternative embodiments, each scheduler unit 510 may include a single dispatch unit 515 or additional dispatch units 515.

Each SM 440 includes a register file 520 that provides a set of registers for the functional units of the SM 440. In one embodiment, the register file 520 is divided between each of the functional units such that each functional unit is allocated a dedicated portion of the register file 520. In another embodiment, the register file 520 is divided between the different warps being executed by the SM 440. The register file 520 provides temporary storage for operands connected to the data paths of the functional units.

Each SM 440 comprises L processing cores 550. In one embodiment, the SM 440 includes a large number (e.g., 128, etc.) of distinct processing cores 550. Each core 550 may include a fully-pipelined, single-precision processing unit that includes a floating point arithmetic logic unit and an integer arithmetic logic unit. The core 550 may also include a double-precision processing unit including a floating point arithmetic logic unit. In one embodiment, the floating point arithmetic logic units implement the IEEE 754-2008 standard for floating point arithmetic. Each SM 440 also comprises M SFUs 552 that perform special functions (e.g., attribute evaluation, reciprocal square root, and the like), and N LSUs 554 that implement load and store operations between the shared memory/L1 cache 570 and the register file 520. In one embodiment, the SM 440 includes 128 cores 550, 32 SFUs 552, and 32 LSUs 554.

Each SM 440 includes an interconnect network 580 that connects each of the functional units to the register file 520 and the LSU 554 to the register file 520, shared memory/L1 cache 570. In one embodiment, the interconnect network 580 is a crossbar that can be configured to connect any of the functional units to any of the registers in the register file 520 and connect the LSUs 554 to the register file and memory locations in shared memory/L1 cache 570.

The shared memory/L1 cache 570 is an array of on-chip memory that allows for data storage and communication between the SM 440 and the primitive engine 435 and between threads in the SM 440. In one embodiment, the shared memory/L1 cache 570 comprises 64 KB of storage capacity and is in the path from the SM 440 to the partition unit 380. The shared memory/L1 cache 570 can be used to cache reads and writes.

The PPU 300 described above may be configured to perform highly parallel computations much faster than conventional CPUs. Parallel computing has advantages in graphics processing, data compression, neural networks, deep learning, biometrics, stream processing algorithms, and the like.

When configured for general purpose parallel computation, a simpler configuration can be used. In this model, as shown in FIG. 3, fixed function graphics processing units are bypassed, creating a much simpler programming model. In this configuration, the work distribution unit 325 assigns and distributes blocks of threads directly to the TPCs 420. The threads in a block execute the same program, using a unique thread ID in the calculation to ensure each thread generates unique results, using the SM 440 to execute the program and perform calculations, shared memory/L1 cache 570 to communicate between threads, and the LSU 554 to read and write Global memory through partition shared memory/L1 cache 570 and partition unit 380. When configured for general purpose parallel computation, the SM 440 can also write commands that scheduler unit 320 can use to launch new work on the TPCs 420.

In one embodiment, the PPU 300 comprises a deep learning or machine learning processor. The PPU 300 is configured to receive commands that specify programs for modeling neural networks and processing data according to a neural network.

In one embodiment, the PPU 300 comprises a graphics processing unit (GPU). The PPU 300 is configured to receive commands that specify shader programs for processing graphics data. Graphics data may be defined as a set of primitives such as points, lines, triangles, quads, triangle strips, and the like. Typically, a primitive includes data that specifies a number of vertices for the primitive (e.g., in a model-space coordinate system) as well as attributes associated with each vertex of the primitive. The PPU 300 can be configured to process the graphics primitives to generate a frame buffer (i.e., pixel data for each of the pixels of the display).

An application writes model data for a scene (i.e., a collection of vertices and attributes) to a memory such as a system memory or memory 304. The model data defines each of the objects that may be visible on a display. The application then makes an API call to the driver kernel that requests the model data to be rendered and displayed. The driver kernel reads the model data and writes commands to the one or more streams to perform operations to process the model data. The commands may reference different shader programs to be implemented on the SMs 440 of the PPU 300 including one or more of a vertex shader, hull shader, domain shader, geometry shader, and a pixel shader. For example, one or more of the SMs 440 may be configured to execute a vertex shader program that processes a number of vertices defined by the model data. In one embodiment, the different SMs 440 may be configured to execute different shader programs concurrently. For example, a first subset of SMs 440 may be configured to execute a vertex shader program while a second subset of SMs 440 may be configured to execute a pixel shader program. The first subset of SMs 440 processes vertex data to produce processed vertex data and writes the processed vertex data to the L2 cache 460 and/or the memory 304. After the processed vertex data is rasterized (i.e., transformed from three-dimensional data into two-dimensional data in screen space) to produce fragment data, the second subset of SMs 440 executes a pixel shader to produce processed fragment data, which is then blended with other processed fragment data and written to the frame buffer in memory 304. The vertex shader program and pixel shader program may execute concurrently, processing different data from the same scene in a pipelined fashion until all of the model data for the scene has been rendered to the frame buffer. Then, the contents of the frame buffer are transmitted to a display controller for display on a display device.

The PPU 300 may be included in a desktop computer, a laptop computer, a tablet computer, a smart-phone (e.g., a wireless, hand-held device), personal digital assistant (PDA), a digital camera, a hand-held electronic device, and the like. In one embodiment, the PPU 300 is embodied on a single semiconductor substrate. In another embodiment, the PPU 300 is included in a system-on-a-chip (SoC) along with one or more other logic units such as a reduced instruction set computer (RISC) CPU, a memory management unit (MMU), a digital-to-analog converter (DAC), and the like.

In one embodiment, the PPU 300 may be included on a graphics card that includes one or more memory devices 304 such as GDDR5 SDRAM. The graphics card may be configured to interface with a PCIe slot on a motherboard of a desktop computer that includes, e.g., a northbridge chipset and a southbridge chipset. In yet another embodiment, the PPU 300 may be an integrated graphics processing unit (iGPU) included in the chipset (i.e., Northbridge) of the motherboard.

Various programs may be executed within the PPU 300 in order to implement the various layers of a neural network. For example, the device driver may launch a kernel on the PPU 300 to implement the neural network on one SM 440 (or multiple SMs 440). The device driver (or the initial kernel executed by the PPU 300) may also launch other kernels on the PPU 300 to perform other layers of the neural network. In addition, some of the layers of the neural network may be implemented on fixed unit hardware implemented within the PPU 300. It will be appreciated that results from one kernel may be processed by one or more intervening fixed function hardware units before being processed by a subsequent kernel on an SM 440.

Exemplary System

Figure 6:
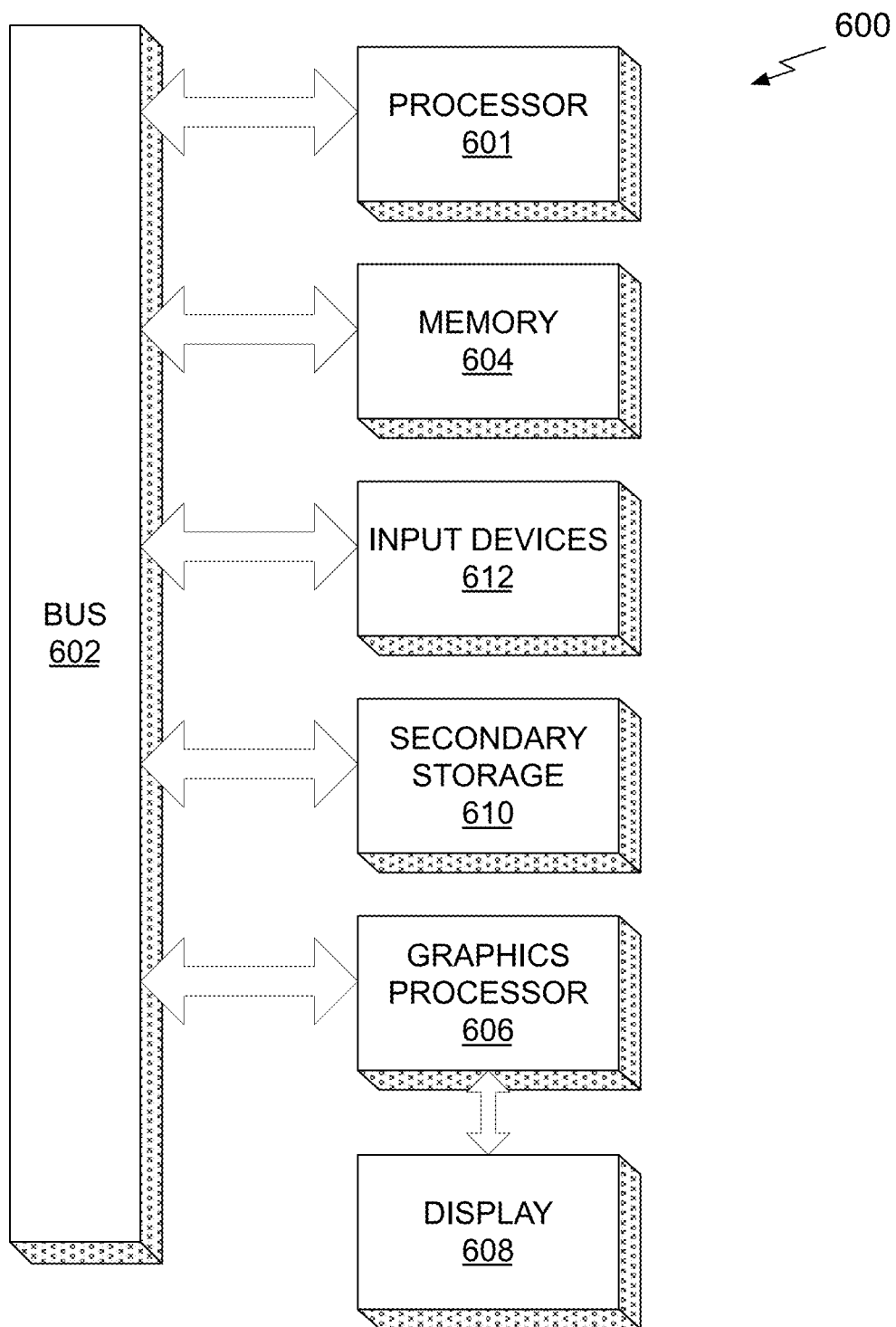
FIG. 6 illustrates an exemplary system in which the various architecture and/or functionality of the various previous embodiments may be implemented.

FIG. 6 illustrates an exemplary system 600 in which the various architecture and/or functionality of the various previous embodiments may be implemented. As shown, a system 600 is provided including at least one central processor 601 that is connected to a communication bus 602. The communication bus 602 may be implemented using any suitable protocol, such as PCI (Peripheral Component Interconnect), PCI-Express, AGP (Accelerated Graphics Port), HyperTransport, or any other bus or point-to-point communication protocol(s). In one embodiment, the communication bus 602 is the system bus 302 shown in FIG. 3. The system 600 also includes a main memory 604. Control logic (software) and data are stored in the main memory 604 which may take the form of random access memory (RAM).

The system 600 also includes input devices 612, a graphics processor 606, and a display 608, i.e. a conventional CRT (cathode ray tube), LCD (liquid crystal display), LED (light emitting diode), plasma display or the like. User input may be received from the input devices 612, e.g., keyboard, mouse, touchpad, microphone, and the like. In one embodiment, the graphics processor 606 may include a plurality of shader modules, a rasterization module, etc. Each of the foregoing modules may even be situated on a single semiconductor platform to form a graphics processing unit (GPU).

In the present description, a single semiconductor platform may refer to a sole unitary semiconductor-based integrated circuit or chip. It should be noted that the term single semiconductor platform may also refer to multi-chip modules with increased connectivity which simulate on-chip operation, and make substantial improvements over utilizing a conventional central processing unit (CPU) and bus implementation. Of course, the various modules may also be situated separately or in various combinations of semiconductor platforms per the desires of the user.

The system 600 may also include a secondary storage 610. The secondary storage 610 includes, for example, a hard disk drive and/or a removable storage drive, representing a floppy disk drive, a magnetic tape drive, a compact disk drive, digital versatile disk (DVD) drive, recording device, universal serial bus (USB) flash memory. The removable storage drive reads from and/or writes to a removable storage unit in a well-known manner.

Computer programs, or computer control logic algorithms, may be stored in the main memory 604 and/or the secondary storage 610. Such computer programs, when executed, enable the system 600 to perform various functions. The memory 604, the storage 610, and/or any other storage are possible examples of computer-readable media.

In one embodiment, the architecture and/or functionality of the various previous figures may be implemented in the context of the central processor 601, the graphics processor 606, an integrated circuit (not shown) that is capable of at least a portion of the capabilities of both the central processor 601 and the graphics processor 606, a chipset (i.e., a group of integrated circuits designed to work and sold as a unit for performing related functions, etc.), and/or any other integrated circuit for that matter.

Still yet, the architecture and/or functionality of the various previous figures may be implemented in the context of a general computer system, a circuit board system, a game console system dedicated for entertainment purposes, an application-specific system, and/or any other desired system. For example, the system 600 may take the form of an autonomous vehicle, desktop computer, laptop computer, server, workstation, game console, embedded system, and/or any other type of logic. Still yet, the system 600 may take the form of various other devices including, but not limited to a personal digital assistant (PDA) device, a mobile phone device, head-mounted display, a television, etc.

Further, while not shown, the system 600 may be coupled to a network (e.g., a telecommunications network, local area network (LAN), wireless network, wide area network (WAN) such as the Internet, peer-to-peer network, cable network, or the like) for communication purposes.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A display system, comprising:
   an optical combiner configured to:
      redirect a first set of light rays towards an eye, wherein the redirected first set of light rays produce a peripheral image; and
      redirect a second set of light rays towards the eye, wherein the redirected second light rays produce an inset foveal image positioned within at least a portion of the peripheral image; and
   a light engine configured to generate the second set of light rays to intersect a first region of the optical combiner and converge at a nodal point within 1 mm of a rotational center the eye and, in response to a change in a gaze direction of the eye, to offset an origin of the second set of light rays to move the intersection of the second set of light rays with the optical combiner from the first region to a second region of the optical combiner.

2. The display system of claim 1, wherein the offset comprises a lateral shift of the light engine.

3. The display system of claim 1, wherein the redirected first set of light rays converge at a second nodal point within the eye.

4. The display system of claim 3, wherein the second nodal point is on a retina of the eye.

5. The display system of claim 3, wherein the second nodal point is between the nodal point and a pupil of the eye.

6. The display system of claim 1, wherein the redirected first set of light rays converge at the nodal point.

7. The display system of claim 1, wherein the optical combiner comprises a single-layer holographic optical element configured to redirect the first and second sets of light rays and transmit other light rays.

8. The display system of claim 1, wherein the optical combiner comprises a holographic optical element having a first layer configured to redirect the first set of light rays and transmit other light rays and a second layer configured to redirect the second set of light rays and transmit the first set of light rays and the other light rays.

9. The display system of claim 1, wherein the light engine comprises a single projector configured to output the first set of light rays during a first duration of time and output the second set of light rays during a second duration of time that does not overlap with the first duration of time.

10. The display system of claim 1, wherein the light engine comprises a first projector configured to output the first set of light rays and a second projector configured to output the second set of light rays.

11. The display system of claim 1, the nodal point is the rotational center of the eye.

12. The display system of claim 1, wherein the redirected first set of light rays converge at a second nodal point within the eye and the peripheral image appears at a different distance from the eye compared with the inset foveal image.

13. The display system of claim 12, wherein the optical combiner is further configured to redirect the first set of light rays from a first region centered at a first point and redirect the second set of light rays from a second region centered at a second point that is within 8 mm of the first point.

14. The display system of claim 1, wherein the redirected first set of light rays are within a first pre-determined wavelength range associated with a first color channel and converge at a second nodal point within the eye and the redirected second set of light rays are within a second pre-determined wavelength range associated with the first color channel.

15. The display system of claim 1, where the first set of light rays are a first wavelength and the second set of light rays are a second wavelength.

16. A computer-implemented method, comprising:
   redirecting a first set of light rays towards an eye, wherein the first set of light rays are redirected by an optical combiner and produce a peripheral image;
   generating a second set of light rays by a light engine to intersect a first region of the optical combiner;
   redirecting the second set of light rays towards the eye, wherein the second set of light rays converge at a nodal point within 1 mm of a rotational center the eye and produce an inset foveal image positioned within at least a portion of the peripheral image; and
   offsetting an origin of the second set of light rays by the light engine to move the intersection of the second set of light rays with the optical combiner from the first region to a second region of the optical combiner in response to a change in a gaze direction of the eye.

17. The computer-implemented method of claim 16, wherein the offset comprises a lateral shift of the light engine.

18. The computer-implemented method of claim 16, wherein the redirected first set of light rays converge at a second nodal point within the eye.

19. The computer-implemented method of claim 16, wherein the redirected first set of light rays converge at the nodal point.

20. A non-transitory, computer-readable storage medium storing instructions that, when executed by a processor, cause the processor to perform steps comprising:
   redirecting a first set of light rays towards an eye, wherein the first set of light rays are redirected by an optical combiner and produce a peripheral image;
   generating a second set of light rays by a light engine to intersect a first region of the optical combiner;
   redirecting the second set of light rays towards the eye, wherein the second set of light rays converge at a nodal point within 1 mm of a rotational center of the eye and produce an inset foveal image positioned within at least a portion of the peripheral image; and
   offsetting an origin of the second set of light rays by the light engine to move the intersection of the second set of light rays with the optical combiner from the first region to a second region of the optical combiner in response to a change in a gaze direction of the eye.

* * * * *